(12) United States Patent
O'Neill et al.

(10) Patent No.: US 6,881,734 B2
(45) Date of Patent: Apr. 19, 2005

(54) PHARMACEUTICAL COMPOSITION FOR THE TREATMENT OF CNS AND OTHER DISORDERS

(75) Inventors: Brian Thomas O'Neill, Old Saybrook, CT (US); Jotham Wadsworth Coe, Niantic, CT (US); Christopher J. O'Donnell, Mystic, CT (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 10/833,714

(22) Filed: Apr. 27, 2004

(65) Prior Publication Data

US 2004/0204416 A1 Oct. 14, 2004

Related U.S. Application Data

(63) Continuation of application No. 10/229,447, filed on Aug. 28, 2002, which is a continuation of application No. 10/047,850, filed on Oct. 23, 2001, now abandoned.
(60) Provisional application No. 60/258,736, filed on Dec. 29, 2000.

(51) Int. Cl.$^7$ .................. C07D 471/08; A61K 31/551; A61P 25/00
(52) U.S. Cl. ....................... 514/221; 540/556
(58) Field of Search ................... 514/221; 540/556

(56) References Cited

FOREIGN PATENT DOCUMENTS

WO        WO 01/92261      *   6/2001

* cited by examiner

*Primary Examiner*—Bruck Kifle
(74) *Attorney, Agent, or Firm*—Peter C. Richardson; Lorraine B. Ling; Eileen M. Ebel

(57) ABSTRACT

The present invention relates to a method of treating disorders of the Central Nervous System (CNS) and other disorders in a mammal, including a human, by administering to the mammal a CNS-penetrant α7 nicotinic receptor agonist. It also relates to pharmaceutical compositions containing a pharmaceutically acceptable carrier and a CNS-penetrant α7 nicotinic receptor agonist.

10 Claims, No Drawings

PHARMACEUTICAL COMPOSITION FOR THE TREATMENT OF CNS AND OTHER DISORDERS

BACKGROUND OF THE INVENTION

The present invention relates to a method of treating disorders of the Central Nervous System (CNS) and other disorders in a mammal, including a human, by administering to the mammal a CNS-penetrant α7 nicotinic receptor agonist. It also relates to pharmaceutical compositions containing a pharmaceutically acceptable carrier and a CNS-penetrant α7 nicotinic receptor agonist.

Schizophrenia is characterized by some or all of the following symptoms: delusions (i.e., thoughts of grandeur, persecution, or control by an outside force), auditory hallucinations, incoherence of thought, loss of association between ideas, marked poverty of speech, and loss of emotional responsiveness. Schizophrenia has long been recognized as a complex disease, which to date has eluded biochemical or genetic characterization. However, recent data in the literature suggest that α7 nicotinic receptor agonists may be therapeutic for this, and other CNS disorders, see: Alder, L. E.; Hoffer, L. D.; Wiser, A.; Freedman, R. *Am. J. Psychiatry* 1993, 150, 1856; Bickford, P. C.; Luntz-Leybman, V.; Freedman, R. *Brain Research,* 1993, 607, 33; Stevens, K. E.; Meltzer, J.; Rose, G. M. *Psychopharmacology* 1995, 119, 163; Freedman, R.; Coon, H.; Myles-Worsley, M.; Orr-Urtreger, A.; Olincy, A.; Davis, A.; Polymeropoulos, M.; Holik, J.; Hopkins, J.; Hoff, M.; Rosenthal, J.; Waldo, M. C.; Reimherr, F.; Wender, P.; Yaw, J.; Young, D. A.; Breese, C. R.; Adams, C.; Patterson, D.; Alder, L. E.; Kruglyak, L.; Leonard, S.; Byerley, W. *Proc. Nat. Acad. Sci. USA* 1997, 94, 587.

The compositions of the present invention that contain an α7 nicotinic receptor agonist are useful for the treatment of depression. As used herein, the term "depression" includes depressive disorders, for example, single episodic or recurrent major depressive disorders, and dysthymic disorders, depressive neurosis, and neurotic depression; melancholic depression including anorexia, weight loss, insomnia and early morning waking, and psychomotor retardation; atypical depression (or reactive depression) including increased appetite, hypersomnia, psychomotor agitation or irritability, anxiety and phobias, seasonal affective disorder, or bipolar disorders or manic depression, for example, bipolar I disorder, bipolar II disorder and cyclothymic disorder.

Other mood disorders encompassed within the term "depression" include dysthymic disorder with early or late onset and with or without atypical features; dementia of the Alzheimer's type, with early or late onset, with depressed mood; vascular dementia with depressed mood, mood disorders induced by alcohol, amphetamines, cocaine, hallucinogens, inhalants, opioids, phencyclidine, sedatives, hypnotics, anxiolytics and other substances; schizoaffective disorder of the depressed type; and adjustment disorder with depressed mood.

The compositions of the present invention that contain an α7 nicotinic receptor agonist are useful for the treatment of anxiety. As used herein, the term "anxiety" includes anxiety disorders, such as panic disorder with or without agoraphobia, agoraphobia without history of panic disorder, specific phobias, for example, specific animal phobias, social phobias, obsessive-compulsive disorder, stress disorders including post-traumatic stress disorder and acute stress disorder, and generalized anxiety disorders.

"Generalized anxiety" is typically defined as an extended period (e.g. at least six months) of excessive anxiety or worry with symptoms on most days of that period. The anxiety and worry is difficult to control and may be accompanied by restlessness, being easily fatigued, difficulty concentrating, irritability, muscle tension, and disturbed sleep.

"Panic disorder" is defined as the presence of recurrent panic attacks followed by at least one month of persistent concern about having another panic attack. A "panic attack" is a discrete period in which there is a sudden onset of intense apprehension, fearfulness or terror. During a panic attack, the individual may experience a variety of symptoms including palpitations, sweating, trembling, shortness of breath, chest pain, nausea and dizziness. Panic disorder may occur with or without agoraphobia.

"Phobias" includes agoraphobia, specific phobias and social phobias. "Agoraphobia" is characterized by an anxiety about being in places or situations from which escape might be difficult or embarrassing or in which help may not be available in the event of a panic attack. Agoraphobia may occur without history of a panic attack. A "specific phobia" is characterized by clinically significant anxiety provoked by feared object or situation. Specific phobias include the following subtypes: animal type, cued by animals or insects; natural environment type, cued by objects in the natural environment, for example storms, heights or water; blood-injection-injury type, cued by the sight of blood or an injury or by seeing or receiving an injection or other invasive medical procedure; situational type, cued by a specific situation such as public transportation, tunnels, bridges, elevators, flying, driving or enclosed spaces; and other type where fear is cued by other stimuli. Specific phobias may also be referred to as simple phobias. A "social phobia" is characterized by clinically significant anxiety provoked by exposure to certain types of social or performance circumstances. Social phobia may also be referred to as social anxiety disorder.

Other anxiety disorders encompassed within the term "anxiety" include anxiety disorders induced by alcohol, amphetamines, caffeine, cannabis, cocaine, hallucinogens, inhalants, phencychdine, sedatives, hypnotics, anxiolytics and other substances, and adjustment disorders with anxiety or with mixed anxiety and depression.

Anxiety may be present with or without other disorders such as depression in mixed anxiety and depressive disorders. The compositions of the present invention are therefore useful in the treatment of anxiety with or without accompanying depression.

By the use of a CNS-penetrant α7 nicotinic receptor agonist in accordance with the present invention, it is possible to treat depression and/or anxiety in patients for whom conventional antidepressant or antianxiety therapy might not be wholly successful or where dependence upon the antidepressant or antianxiety therapy is prevalent.

SUMMARY OF THE INVENTION

This invention relates to compounds of the formula I

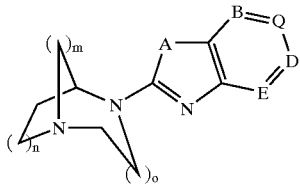

wherein n =1–2;
m=1–2;
o=1–2;
A=O, S or NR$^1$;
B=N or CR$^2$;
Q=N or CR$^3$;
D=N or CR$^4$;
E=N or CR$^5$;
R$^1$ is H, a straight chain or branched (C$_1$–C$_8$)alkyl, C(=O)OR$^6$, CH$_2$R$^6$, C(=O)NR$^6$R$^7$, C(=O)R$^6$, or SO$_2$R$^6$;
each R$^2$, R$^3$, R$^4$ and R$^5$ is independently selected from F, Cl, Br, I, nitro, cyano, CF$_3$, —NR$^6$R$^7$, —NR$^6$C(=O)R$^7$, —NR$^6$C(=O)NR$^7$R$^8$, —NR$^6$C(=O)OR$^7$, —NR$^6$S(=O)$_2$R$^7$, —NR$^6$S(=O)$_2$NR$^7$R$^8$, —OR, —OC(=O)R$^6$, —OC(=O)OR$^6$, —OC(=O)NR$^6$R$^7$, —OC(=O)SR$^6$, —C(=O)OR$^6$, —C(=O)R$^6$, —C(=O)NR$^6$R$^7$, —SR$^6$, —S(=O)R$^6$, —S(=O)$_2$R$^6$, —S(=O)$_2$NR$^6$R$^7$, and R$^6$;
each R$^6$, R$^7$, and R$^8$ is independently selected from H, straight chain or branched (C$_1$–C$_8$)alkyl, straight chain or branched (C$_2$–C$_8$)alkenyl, straight chain or branched (C$_2$–C$_8$)alkynyl, (C$_3$–C$_8$)cycloalkyl, (C$_4$–C$_8$)cycloalkenyl, 3–8 membered heterocycloalkyl, (C$_5$–C$_{11}$)bicycloalkyl, (C$_7$–C$_{11}$)bicycloalkenyl, 5–11 membered heterobicycloalkyl, 5–11 membered heterobicycloalkenyl, (C$_6$–C$_{11}$) aryl, and 5–12 membered heteroaryl; wherein each R$^6$, R$^7$, and R$^8$ is optionally substituted with from one to six substituents, independently selected from F, Cl, Br, I, nitro, cyano, CF$_3$, —NR$^9$R$^{10}$, —NR$^9$C(=O)R$^{10}$, —NR$^9$C(=O)NR$^{10}$R$^{11}$, —NR$^9$C(=O)OR$^{10}$, —NR$^9$S(=O)$_2$R$^{10}$, —NR$^9$S(=O)$_2$NR$^{10}$R$^{11}$, —OR$^9$, —OC(=O)R$^9$, —OC(=O)OR$^9$, —OC(=O)NR$^9$R$^{10}$, —OC(=O)SR$^9$, —C(=O)OR$^9$, —C(=O)R$^9$, —C(=O)NR$^9$R$^{10}$, —SR$^9$, —S(=O)R$^9$, —S(=O)$_2$R$^9$, —S(=O)$_2$NR$^9$R$^{10}$ and R$^9$;
each R$^9$, R$^{10}$ and R$^{11}$ is independently selected from H, straight chain or branched (C$_1$–C$_8$)alkyl, straight chain or branched (C$_2$–C$_8$)alkenyl, straight chain or branched (C$_2$–C$_8$)alkynyl, (C$_3$–C$_8$)cycloalkyl, (C$_4$–C$_8$)cycloalkenyl, 3–8 membered heterocycloalkyl, (C$_5$–C$_{11}$)bicycloalkyl, (C$_7$–C$_{11}$)bicycloalkenyl, 5–11 membered heterobicycloalkyl, (5–11 membered) heterobicycloalkenyl, (C$_6$–C$_{11}$)aryl or 5–12 membered heteroaryl; wherein each R$^9$, R$^{10}$ and R$^{11}$ is optionally substituted with from one to six substituents independently selected from F, Cl, Br, I, nitro, cyano, CF$_3$, —NR$^{12}$R$^{13}$, —NR$^{12}$C(=O)R$^{13}$, —NR$^{12}$C(=O)NR$^{13}$R$^{14}$, —NR$^{12}$C(=O)OR$^{13}$, —NR$^{12}$S(=O)$_2$R$^{13}$, —NR$^{12}$S(=O)$_2$NR$^{13}$R$^{14}$, —OR$^{12}$, —OC(=O)R$^{12}$, —OC(=O)OR$^{12}$, —OC(=O)NR$^{12}$R$^{13}$, —OC(=O)SR$^{12}$, —C(=O)OR$^{12}$, —C(=O)R$^{12}$, —C(=O)NR$^{12}$R$^{13}$, —SR$^{12}$, —S(=O)R$^{12}$, —S(=O)$_2$R$^{12}$, —S(=O)$_2$NR$^{12}$R$^{13}$ and R$^{12}$;
each R$^{12}$, R$^{13}$, and R$^{14}$ is independently selected from H, straight chain or branched (C$_1$–C$_8$)alkyl, straight chain or branched (C$_2$–C$_8$)alkenyl, straight chain or branched (C$_2$–C$_8$)alkynyl, (C$_3$–C$_8$)cycloalkyl, (C$_4$–C$_8$)cycloalkenyl, 3–8 membered heterocycloalkyl, (C$_5$–C$_{11}$)bicycloalkyl, (C$_7$–C$_{11}$)bicycloalkenyl, 5–11 membered heterobicycloalkyl, 5–11 membered heterobicycloalkenyl, (C$_6$–C$_{11}$) aryl and (5–12 membered) heteroaryl;
or R$^2$ and R$^3$, or R$^3$ and R$^4$, or R$^4$ and R$^5$, may form another 6-membered aromatic or heteroaromatic ring sharing B and Q, or Q and D, or D and E, respectively, and may be optionally substituted with from one to four substitutuents independently selected from the group of radicals set forth in the definition of R$^6$, R$^7$ and R$^8$ above;
and all enantiomeric, diastereomeric, and tautomeric isomers and pharmaceutically acceptable salts thereof.

More specific embodiments of this invention relate to compounds of the formula I wherein n=1, m=2, and o=1.

More specific embodiments of this invention relate to compounds of the formula I wherein A=S.

More specific embodiments of this invention relate to compounds of the formula I wherein A=NR$^1$.

More specific embodiments of this invention relate to compounds of the formula I wherein A=O.

More specific embodiments of this invention relate to compounds of the formula I wherein A=O, B=CR$^2$, Q=CR$^3$, D=CR$^4$, E=CR$^5$.

More specific embodiments of this invention relate to compounds of the formula I wherein A=O, B=N, Q=CR$^3$, D=CR$^4$, E=CR$^5$.

More specific embodiments of this invention relate to compounds of the formula I wherein A=O, B=CR$^2$, Q=N, D=CR$^4$, E=CR$^5$.

More specific embodiments of this invention relate to compounds of the formula I wherein A=O, B=CR$^2$, Q=CR$^3$, D=N, E=CR$^5$.

More specific embodiments of this invention relate to compounds of the formula I wherein A=O, B=CR$^2$, Q=CR$^3$, D=CR$^4$, E=N.

The term "alkyl", as used herein, unless otherwise indicated, includes saturated monovalent hydrocarbon radicals having straight or branched moieties. Examples of alkyl groups include, but are not limited to, methyl, ethyl, propyl, isopropyl, and t-butyl.

The term "alkenyl", as used herein, unless otherwise indicated, includes alkyl moieties having at least one carbon-carbon double bond wherein alkyl is as defined above. Examples of alkenyl include, but are not limited to, ethenyl and propenyl.

The term "alkynyl", as used herein, unless otherwise indicated, includes alkyl moieties having at least one carbon-carbon triple bond wherein alkyl is as defined above. Examples of alkynyl groups include, but are not limited to, ethynyl and 2-propynyl.

The term "cycloalkyl", as used herein, unless otherwise indicated, includes non-aromatic saturated cyclic alkyl moieties wherein alkyl is as defined above. Examples of cycloalkyl include, but are not limited to, cyclopropyl, cyclobutyl, cyclopentyl, cyclohexyl, and cycloheptyl. "Bicycloalkyl" groups are non-aromatic saturated carbocyclic groups consisting of two rings. Examples of bicycloalkyl groups include, but are not limited to, bicyclo-[2.2.2]-octyl and norbornyl. The term "cycloalkenyl" and "bicycloalkenyl" refer to non-aromatic carbocyclic cycloalkyl and bicycloalkyl moieties as defined above, except comprising of one or more carbon-carbon double bonds connecting carbon ring members (an "endocyclic" double bond) and/or one or more carbon-carbon double bonds connecting a carbon ring member and an adjacent non-ring carbon (an "exocyclic" double bond). Examples of cycloalkenyl groups include, but are not limited to, cyclopentenyl and cyclohexenyl. A non-limiting example of a bicycloalkenyl group is norborenyl. Cycloalkyl, cycloalkenyl, bicycloalkyl, and bicycloalkenyl groups also include groups similar to those described above for each of these respective categories, but which are substituted with one or more oxo moieties. Examples of such groups with oxo moieties include, but are not limited to oxocyclopentyl, oxocyclobutyl, oxocyclopentenyl, and norcamphoryl.

The term "aryl", as used herein, unless otherwise indicated, includes an organic radical derived from an aromatic hydrocarbon by removal of one hydrogen atom. Examples of aryl groups include, but are not limited to phenyl and naphthyl.

The terms "heterocyclic" and "heterocycloalkyl", as used herein, refer to non-aromatic cyclic groups containing one or more heteroatoms, preferably from one to four heteroatoms, each selected from O, S and N. "Heterobicycloalkyl" groups are non-aromatic two-ringed cyclic groups, wherein at least one of the rings contains a heteroatom (O, S, or N). The heterocyclic groups of this invention can also include ring systems substituted with one or more oxo moieties. Examples of non-aromatic heterocyclic groups include, but are not limited to, aziridinyl, azetidinyl, pyrrolidinyl, piperidinyl, azepinyl, piperazinyl, 1,2,3,6-tetrahydropyridinyl, oxiranyl, oxetanyl, tetrahydrofuranyl, tetrahydropyranyl, tetrahydrothienyl, tetrahydrothiopyranyl, piperidino, morpholino, thiomorpholino, thioxanyl, pyrrolinyl, indolinyl, 2H-pyranyl, 4H-pyranyl, dioxanyl, 1,3-dioxolanyl, pyrazolinyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl, quinuclidinyl and quinolizinyl.

The term "heteroaryl", as used herein, refers to aromatic groups containing one or more heteroatoms (O, S, or N). A multicyclic group containing one or more heteroatoms wherein at least one ring of the group is aromatic is a "heteroaryl" group. The heteroaryl groups of this invention can also include ring systems substituted with one or more oxo moieties. Examples of heteroaryl groups include, but are not limited to, pyridinyl, pyridazinyl, imidazolyl, pyrimidinyl, pyrazolyl, triazolyl, pyrazinyl, quinolyl, isoquinolyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, purinyl, oxadiazolyl, thiazolyl, thiadiazolyl, furazanyl, benzofurazanyl, benzothiophenyl, benzotriazolyl, benzothiazolyl, benzoxazolyl, quinazolinyl, quinoxalinyl, naphthyridinyl, dihydroquinolyl, tetrahydroquinolyl, dihydroisoquinolyl, tetrahydroisoquinolyl, benzofuryl, furopyridinyl, pyrolopyrimidinyl, and azaindolyl.

The foregoing heteroaryl, heterocyclic and heterocycloalkyl groups may be C-attached or N-attached (where such is possible). For instance, a group derived from pyrrole may be pyrrol-1-yl (N-attached) or pyrrol-3-yl (C-attached).

Examples of specific compounds of this invention are the following compounds of the formula I and their pharmaceutically acceptable salts, hydrates, solvates and optical and other stereoisomers:

4-Benzooxazol-2-yl-1,4-diaza-bicyclo[3.2.2]nonane;
2-(1,4-Diaza-bicyclo[3.2.2]non-4-yl)-1-oxa-3-aza-cyclopenta[b]-naphthalene;
4-Benzothiazol-2-yl-1,4-diaza-bicyclo[3.2.2]nonane;
4-(5-Phenyl-benzooxazol-2-yl)-1,4-diaza-bicyclo[3.2.2]nonane;
4-(1H-Benzoimidazol-2-yl)-1,4-diaza-bicyclo[3.2.2]nonane;
4-(6-Phenyl-benzooxazol-2-yl)-1,4-diaza-bicyclo[3.2.2]nonane;
2-(1,4-Diaza-bicyclo[3.2.2]non-4-yl)-3-oxa-1-aza-cyclopenta[a]-naphthalene;
4-(5-Chloro-benzooxazol-2-yl )-1,4-diaza-bicyclo[3.2.2]nonane;
4-(5-Fluoro-benzooxazol-2-yl)-1,4-diaza-bicyclo[3.2.2]nonane;
4-(6-Nitro-benzooxazol-2-yl )-1,4-diaza-bicyclo[3.2.2]nonane;
4-Oxazolo[5,4-b]pyridin-2-yl-1,4-diaza-bicyclo[3.2.2]nonane;
4-Oxazolo[5,4-c]pyridin-2-yl-1,4-diaza-bicyclo[3.2.2]nonane;
4-Oxazolo[4,5-c]pyridin-2-yl-1,4-diaza-bicyclo[3.2.2]nonane;
4-Oxazolo[4,5-b]pyridin-2-yl-1,4-diaza-bicyclo[3.2.2]nonane;
4-(5-Pyridin-3-yl-benzooxazol-2-yl)-1,4-diaza-bicyclo[3.2.2]-nonane;
4-(5-Bromo-benzooxazol-2-yl)-1,4-diaza-bicyclo[3.2.2]nonane;
4-(6-Bromo-oxazolo[5,4-b]pyridin-2-yl)-1,4-diaza-bicyclo[3.2.2]-nonane;
4-(5-Iodo-benzooxazol-2-yl )-1,4-diaza-bicyclo[3.2.2]nonane;
4-(4-Nitro-benzooxazol-2-yl )-1,4-diaza-bicyclo[3.2.2]nonane;
4-(5-Nitro-benzooxazol-2-yl )-1,4-diaza-bicyclo[3.2.2]nonane;
4-(5-Methyl-benzooxazol-2-yl)-1,4-diaza-bicyclo[3.2.2]nonane;
4-(6-Methyl-benzooxazol-2-yl)-1,4-diaza-bicyclo[3.2.2]nonane;
4-(5-Methyl-oxazolo[4,5-b]pyridin-2-yl)-1,4-diaza-bicyclo[3.2.2]nonane;
4-(6-Chloro-5-nitro-benzooxazol-2-yl)-1,4-diaza-bicyclo[3.2.2]nonane;
4-(5-Chloro-6-nitro-benzooxazol-2-yl)-1,4-diaza-bicyclo[3.2.2]nonane;
Benzyl-[2-(1,4-diaza-bicyclo[3.2.2]non-4-yl)-benzooxazol-5-yl]-amine;
[2-(1,4-Diaza-bicyclo[3.2.2]non-4-yl)-benzooxazol-5-yl]-(3-phenyl-allyl)-amine; [2-(1,4-Diaza-bicyclo[3.2.2]non-4-yl)-benzooxazol-5-yl]-pyridin-3-ylmethyl-amine;
Dibenzyl-[2-(1,4-diaza-bicyclo[3.2.2]non4-yl)-benzooxazol-5-yl]-amine;
4-(5-m-Tolyl-benzooxazol-2-yl)-1,4-diaza-bicyclo[3.2.2]nonane;
4-(6-Phenyl-oxazolo[5,4-b]pyridin-2-yl)-1,4-diaza-bicyclo[3.2.2]nonane;
4-[5-(4-Trifluoromethyl-phenyl)-benzooxazol-2-yl]-1,4-diaza-bicyclo[3.2.2]nonane;
4-(6-Bromo-oxazolo[4,5-b]pyridin-2-yl)-1,4-diaza-bicyclo[3.2.2]nonane;
4-(6-Phenyl-oxazolo[4,5-b]pyridin-2-yl)-1,4-diaza-bicyclo[3.2.2]nonane; and
4-(5,7-Dichloro-benzooxazol-2-yl)-1,4-diaza-bicyclo[3.2.2]nonane.

Unless otherwise indicated, the term "one or more substituents", as used herein, refers to from one to the maximum number of substituents possible based on the number of available bonding sites.

The term "treatment", as used herein, refers to reversing, alleviating, inhibiting the progress of, or preventing the disorder or condition to which such term applies, or one or more symptoms of such condition or disorder. The term "treatment", as used herein, refers to the act of treating, as "treating" is defined immediately above.

Compounds of formula I may contain chiral centers and therefore may exist in different enantiomeric and diastereomeric forms. Individual isomers can be obtained by known methods, such as optical resolution, optically selective reaction, or chromatographic separation in the preparation of the final product or its intermediate. This invention relates to all optical isomers and all stereoisomers of compounds of the formula I, both as racemic mixtures and as individual enantiomers and diastereoismers of such compounds, and mixtures thereof, and to all pharmaceutical compositions and methods of treatment defined above that contain or employ them, respectively.

In so far as the compounds of formula I of this invention are basic compounds, they are all capable of forming a wide variety of different salts with various inorganic and organic acids. Although such salts must be pharmaceutically acceptable for administration to animals, it is often desirable in practice to initially isolate the base compound from the reaction mixture as a pharmaceutically unacceptable salt and then simply convert to the free base compound by treatment with an alkaline reagent and thereafter convert the free base to a pharmaceutically acceptable acid addition salt. The acid addition salts of the base compounds of this invention are readily prepared by treating the base compound with a substantially equivalent amount of the chosen mineral or organic acid in an aqueous solvent or in a suitable organic solvent, such as methanol or ethanol. Upon careful evaporation of the solvent, the desired solid salt is readily obtained. The acids which are used to prepare the pharmaceutically acceptable acid addition salts of the aforementioned base compounds of this invention are those which form non-toxic acid addition salts, i.e., salts containing pharmaceutically acceptable anions, such as the hydrochloride, hydrobromide, hydroiodide, nitrate, sulfate or bisulfate, phosphate or acid phosphate, acetate, lactate, citrate or acid citrate, tartrate or bi-tartrate, succinate, maleate, fumarate, gluconate, saccharate, benzoate, methanesulfonate, ethanesulfonate, benzenesulfonate, p-toluenesulfonate and pamoate (i.e., 1,1'-methylene-bis-(2-hydroxy-3-naphthoate))salts.

The present invention also includes isotopically labelled compounds, which are identical to those recited in formula I, but for the fact that one or more atoms are replaced by an atom having an atomic mass or mass number different from the atomic mass or mass number usually found in nature. Examples of isotopes that can be incorporated into compounds of the present invention include isotopes of hydrogen, carbon, nitrogen, oxygen, phosphorous, sulfur, fluorine and chlorine, such as $^2$H, $^3$H, $^{13}$C, $^{11}$C, $^{14}$C, $^{15}$N, $^{18}$O, $^{17}$O, $^{31}$P, $^{32}$P, $^{35}$S, $^{18}$F, and $^{36}$Cl, respectively. Compounds of the present invention, prodrugs thereof, and pharmaceutically acceptable salts of said compounds or of said prodrugs which contain the aforementioned isotopes and/or other isotopes of other atoms are within the scope of this invention. Certain isotopically labelled compounds of the present invention, for example those into which radioactive isotopes such as $^3$H and $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detectability. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically labelled compounds of formula I of this invention and prodrugs thereof can generally be prepared by carrying out the procedures disclosed in the Schemes and/or in the Examples and Preparations below, by substituting a readily available isotopically labelled reagent for a non-isotopically labelled reagent.

The present invention also relates to a pharmaceutical composition for the treatment of schizophrenia in a mammal, including a human, comprising an amount of a compound of the formula I, or a pharmaceutically acceptable salt thereof, that is effective in treating schizophrenia and a pharmaceutically acceptable carrier.

The present invention also relates to a method of treating schizophrenia in a mammal, including a human, comprising administering to said mammal an amount of a compound of the formula I, or a pharmaceutically acceptable salt thereof, that is effective in treating schizophrenia.

The present invention also relates to a pharmaceutical composition for the treatment of schizophrenia in a mammal, including a human, comprising an α7 nicotinic receptor agonist compound of the formula I, or a pharmaceutically acceptable salt thereof, and a pharmaceutically acceptable carrier.

The present invention also relates to a method of treating schizophrenia in a mammal, including a human, comprising administering to said mammal an α7 nicotinic receptor agonizing amount of a compound of the formula I, or a pharmaceutically acceptable salt thereof.

The present invention also relates to a pharmaceutical composition for treating a disorder or condition selected from inflammatory bowel disease (including but not limited to ulcerative colitis, pyoderma gangrenosum and Crohn's disease), irritable bowel syndrome, spastic dystonia, chronic pain, acute pain, celiac sprue, pouchitis, vasoconstriction, anxiety, panic disorder, depression, bipolar disorder, autism, sleep disorders, jet lag, amylotropic lateral sclerosis (ALS), cognitive dysfunction, tinnitus, hypertension, bulimia, anorexia, obesity, cardiac arrythmias, gastric acid hypersecretion, ulcers, pheochromocytoma, progressive supramuscular palsy, chemical dependencies and addictions (e.g., dependencies on, or addictions to nicotine (and/or tobacco products), alcohol, benzodiazepines, barbiturates, opioids or cocaine), headache, stroke, traumatic brain injury (TBI), psychosis, Huntington's Chorea, tardive dyskinesia, hyperkinesia, dyslexia, multi-infarct dementia, age related cognitive decline, epilepsy, including petit mal absence epilepsy, senile dementia of the Alzheimer's type (AD), Parkinson's disease (PD), attention deficit hyperactivity disorder (ADHD) and Tourette's Syndrome in a mammal, comprising an amount of a compound of the formula I, or a pharmaceutically acceptable salt thereof, that is effective in treating such disorder or condition and a pharmaceutically acceptable carrier.

The present invention also relates to a method of treating a disorder or condition selected from inflammatory bowel disease (including but not limited to ulcerative colitis, pyoderma gangrenosum and Crohn's disease), irritable bowel syndrome, spastic dystonia, chronic pain, acute pain, celiac sprue, pouchitis, vasoconstriction, anxiety, panic disorder, depression, bipolar disorder, autism, sleep disorders, jet lag, amyotropic lateral sclerosis (ALS), cognitive dysfunction, tinnitus, hypertension, bulimia, anorexia, obesity, cardiac arrythmias, gastric acid hypersecretion, ulcers, pheochromocytoma, progressive supramuscular palsy, chemical dependencies and addictions (e.g., dependencies on, or addictions to nicotine (and/or tobacco products), alcohol, benzodiazepines, barbiturates, opioids or cocaine), headache, stroke, traumatic brain injury (TBI), psychosis, Huntington's Chorea, tardive dyskinesia, hyperkinesia, dyslexia, multi-infarct dementia, age related cognitive decline, epilepsy, including petit mal absence epilepsy, senile dementia of the Alzheimer's type (AD), Parkinson's disease (PD), attention deficit hyperactivity disorder (ADHD) and Tourette's Syndrome in a mammal, comprising administering to a mammal in need of such treatment an amount of a compound of the formula I, or a pharmaceutically acceptable salt thereof, that is effective in treating such disorder or condition.

The present invention also relates to a pharmaceutical composition for treating a disorder or condition selected from inflammatory bowel disease (including but not limited to ulcerative colitis, pyoderma gangrenosum and Crohn's disease), irritable bowel syndrome, spastic dystonia, chronic pain, acute pain, celiac sprue, pouchitis, vasoconstriction, anxiety, panic disorder, depression, bipolar disorder, autism, sleep disorders, jet lag, amyotropic lateral sclerosis (ALS), cognitive dysfunction, tinnitus, hypertension, bulimia, anorexia, obesity, cardiac arrythmias, gastric acid hypersecretion, ulcers, pheochromocytoma, progressive supramuscular palsy, chemical dependencies and addictions (e.g., dependencies on, or addictions to nicotine (and/or tobacco products), alcohol, benzodiazepines, barbituates, opioids or cocaine), headache, stroke, traumatic brain injury (TBI), psychosis, Huntington's Chorea, tardive dyskinesia, hyperkinesia, dyslexia, multi-infarct dementia, age related cognitive decline, epilepsy, including petit mal absence epilepsy, senile dementia of the Alzheimer's type (AD), Parkinson's disease (PD), attention deficit hyperactivity disorder (ADHD) and Tourefte's Syndrome in a mammal, comprising an α7 nicotinic receptor agonizing amount of a compound of the formula I, or a pharmaceutically acceptable salt thereof, and a pharmaceutically acceptable carrier.

The present invention also relates to a method of treating a disorder or condition selected from inflammatory bowel disease (including but not limited to ulcerative colitis, pyoderma gangrenosum and Crohn's disease), irritable bowel syndrome, spastic dystonia, chronic pain, acute pain, celiac sprue, pouchitis, vasoconstriction, anxiety, panic disorder, depression, bipolar disorder, autism, sleep disorders, jet lag, amyotropic lateral sclerosis (ALS), cognitive dysfunction, tinnitus, hypertension, bulimia, anorexia, obesity, cardiac arrythmias, gastric acid hypersecretion, ulcers, pheochromocytoma, progressive supramuscular palsy, chemical dependencies and addictions (, dependencies on, or addictions to nicotine (and/or tobacco products), alcohol, benzodiazepines, barbituates, opioids or cocaine), headache, stroke, traumatic brain injury (TBI), psychosis, Huntington's Chorea, tardive dyskinesia, hyperkinesia, dyslexia, multi-infarct dementia, age related cognitive decline, epilepsy, including petit mal absence epilepsy, senile dementia of the Alzheimer's type (AD), Parkinson's disease (PD), attention deficit hyperactivity disorder (ADHD) and Tourette's Syndrome in a mammal, comprising administering to a mammal in need of such treatment an α7 nicotinic receptor agonizing amount of a compound of the formula I, or a pharmaceutically acceptable salt thereof.

DETAILED DESCRIPTION OF THE INVENTION

Compounds of the formula I can be readily prepared according to the methods described below. In the reaction schemes and discussion that follow, m, n, o, A, B, Q, D, and E, unless otherwise indicated, are defined as they are above in the definition of compounds of the formula I.

As used herein, the expression "inert reaction solvent" refers to a solvent system in which the components do not interact with starting materials, reagents, or intermediates of products in a manner which adversely affects the yield of the desired product.

During any of the following synthetic sequences it may be necessary and/or desirable to protect sensitive or reactive groups on any of the molecules concerned. This may be achieved by means of conventional protecting groups, such as those described in T. W. Greene and P. G. M. Wuts, *Protective Groups in Organic Synthesis*, John Wiley & Sons, 1999.

Scheme 1

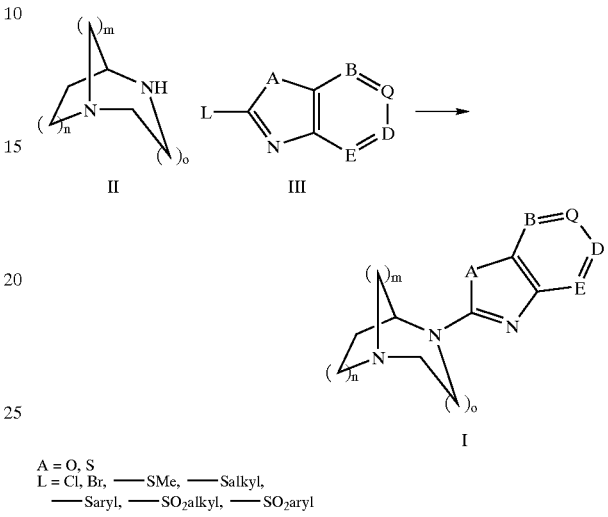

A = O, S
L = Cl, Br, —SMe, —Salkyl,
—Saryl, —SO$_2$alkyl, —SO$_2$aryl

Compounds of the formula I wherein A is an oxygen or sulfur atom can be prepared as illustrated in Scheme 1. Referring to Scheme 1, a compound of the formula II is reacted with a compound of the formula III wherein A is oxygen or sulfur and L is a leaving group (e.g., choride, bromide, methyl sulfide, alkyl sulfide, aryl sulfide, alkyl sulfoxide, or aryl sulfoxide) in the presence or absence of base (e.g., triethylamine, diisopropylamine, pyridine, 2,6-lutidine, sodium or potassium hydroxide, sodium or potassium or cesium carbonate, sodium or potassium tert-butoxide, diisopropylethylamine, or 1,8-diazabicyclo[5.4.0]undec-7-ene) in the presence or absence of an inert reaction solvent such as water, methanol, ethanol, isopropanol, acetonitrile, methylene chloride, chloroform, 1,2-dichloroethane, tetrahydrofuran, diethylether, dioxane, 1,2-dimethoxyethane, benzene, toluene, dimethylformamide, or dimethylsulfoxide. This reaction is typically carried out at a temperature from about −10° C. to about 150° C. In one set of preferred conditions, when A is oxygen, L is methylsulfide and the reaction is carried out in the absence of solvent at a temperature from about 70° C. to about 120° C. In a second set of preferred conditions, when A is oxygen, L is chloride and the reaction is carried out in the presence of triethylamine, diisopropylethylamine, or sodium tert-butoxide in a solvent selected from chloroform, methylene chloride and toluene at a temperature from about 0° C. to about 50° C.

Scheme 2

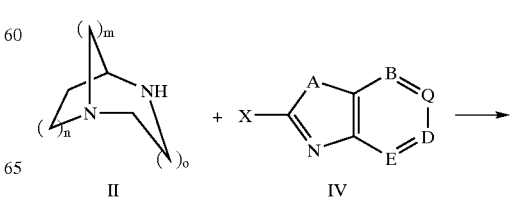

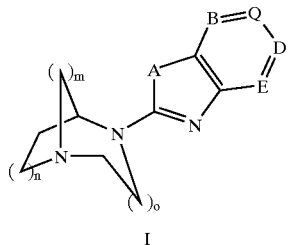

A = NR¹
X = Cl, Br, I, OTf

Compounds of the formula I wherein A is NR¹ can be prepared as illustrated in Scheme 2. Referring to Scheme 2, treatment of a compound of the formula II with a compound of the formula IV wherein X is equal to chlorine, bromine, iodine or trimethylmethanesulfonate, preferably chlorine or bromine, affords the desired compound of formula I. This reaction is generally carried out using a palladium catalyst such as palladium (0) tetrakis(triphenylphosphine), palladium (II) acetate, allyl palladium chloride dimer, tris(dibenzylideneacetone)dipalladium (0), tris(dibenzylideneacetone)dipalladium (0) chloroform adduct, palladium (II) chloride or dichloro[1,1'-bis(diphenylphosphino)ferrocene]palladium (II) dichloromethane adduct, preferably tris(dibenzylideneacetone)dipalladium (0), in the presence or absence of a phosphine ligand such as 1,1'-bis(diphenylphosphino)ferrocene, triphenylphosphine, tri-o-tolylphosphine, tri-tert-butylphosphine, 1,2-bis(diphenylphosphino)ethane, 1,3-bis(diphenylphosphino)propane, 2,2'-bis(diphenylphosphino)-1,1'-binaphthyl, 2-biphenyl dicyclohexylphosphine, 2-biphenyl-di-tert-butylphosphine, 2-(N,N-dimethylamino)-2'-di-tert-butylphosphinobiphenyl or 2-(N,N-dimethylamino)-2'-dicyclohexylphosphinobiphenyl, preferably 2,2'-bis(diphenylphosphino)-1,1'-binaphthyl, in the presence of a base such as potassium acetate, sodium acetate, cesium acetate, sodium tert-butoxide, potassium tert-butoxide, sodium carbonate, lithium carbonate, potassium carbonate, cesium carbonate or cesium fluoride, preferably sodium tert-butoxide. Suitable reaction inert solvents for this reaction include, but are not limited to, 1,4-dioxane, acetonitrile, methyl sulfoxide, tetrahydrofuran, ethanol, methanol, 2-propanol and toluene. The preferred solvent is toluene. Suitable reaction temperatures can range from about 0° C. to about 200° C., and are preferably from about 80° C. to about 120° C.

Compounds of the formula II can be prepared using methods analogous to those reported in the literature, see: Rubstov, M. V.; Mikhlina, E. E.; Vorob'eva, V. Ya.; Yanina, A. Zh. Obshch. Khim. (1964), V34, 2222–2226. Compounds of formula III and formula IV can also be prepared by methods analogous to those reported in the literature, see: Lok, R.; Leone, R. E.; Williams, A. J. J. Org. Chem. (1996), 61, 3289–3297; Yamato, M.; Takeuchi, Y.; Hashigaki, K.; Hirota, T. Chem. Pharm. Bull. (1983), 31, 733–736; Chu-Moyer, M. Y.; Berger, R. J. Org. Chem. (1995), 60, 5721–5725; Sato, Y.; Yamada, M.; Yoshida, S.; Soneda, T.; Ishikawa, M.; Nizato, T.; Suzuki, K.; Konno, F. J. Med. Chem. (1998), 41, 3015–3021 and Van Allan, J. A.; Deacon, B. D. Organic Syntheses; Wiley: New York (1963); Collect. Vol. IV, pp 569–70.

Scheme 3

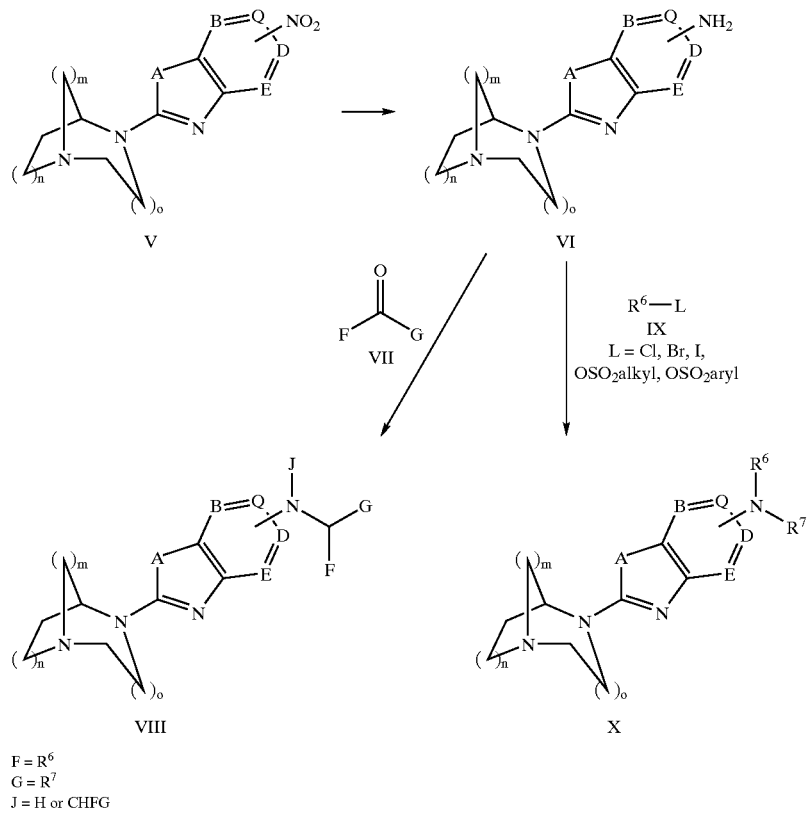

Compounds of the formula I wherein one of the substituents on B, Q, D or E is equal to NR⁶R⁷ can be prepared as illustrated in Scheme 3. Referring to Scheme 3, treatment of a compound of formula V wherein one of the substituents on B, Q, D or E is substituted with a nitro group with reducing conditions such as but not limited to zinc, tin or iron and acid, catalytic hydrogenation, tranfer hydrogenolysis or sodium hydrosulfite in an inert reaction solvent such as water, methanol, ethanol, isopropanol, with the preferred conditions being catalytic hydrogenation using palladium on carbon as a catalyst in ethanol at ambient temperature and 50 psi of hyrdogen affords a compound of formula VI wherin the nitro group has been converted to a primary amine. The compound of formula VI can then be treated with a compound of formula VII wherein F and G are defined as R⁶ and R⁷ above and a reducing agent such as but not limited to sodium triacetoxyborohydride, sodium borohydride, sodium cyanoborohydride, lithium aluminum hydride, catalytic hydrogenation or transfer hydrogenolysis in the presence or absence of an acid such as but not limited to acetic acid, hydrochloric acid, trifluoroacetic acid, sulfuric acid, phosphoric acid or nitric acid in an inert reaction solvent such as chloroform, dichloromethane, 1,2-dichloroethane, acetonitrile, toluene, benzene, ethanol, methanol or water at 0° C. to 100° C. with the preferred conditions being sodium triacetoxyborohydride in 1,2-dichloroethane at 25° C. to 90° C. to afford a compound of formula VIII.

Also referring to Scheme 3, a compound of formula VI and be reacted with a compound of formula IX in which R⁶ is as defined above and L is a leaving group (e.g., Cl, Br, I, OSO₂alkyl, OSO₂aryl) in the presence or absence of base (e.g., sodium or potassium hydroxide, sodium or potassium or cesium carbonate, sodium or potassium tert-butoxide, sodium or potassium hydrogen carbonate, sodium or potassium acetate) in the presence or absence of an inert reaction solvent such as water, methanol, ethanol, isopropanol, acetonitrile, methylene chloride, chloroform, 1,2-dichloroethane, tetrahydrofuran, diethylether, dioxane, 1,2-dimethoxyethane, benzene, toluene, dimethylformamide, or dimethylsulfoxide at a temperature from about −10° C. to about 150° C. to produce a compound of formula X. The preferred condition are L=Br, in ethanol at 25° C. to 78° C.

Scheme 4

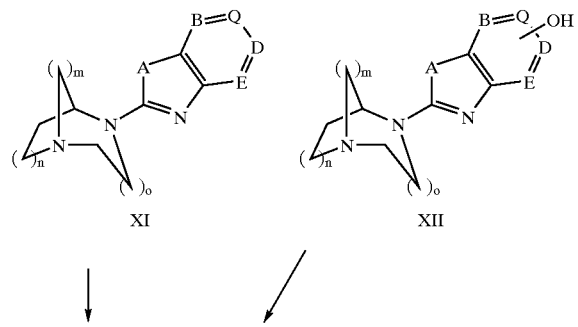

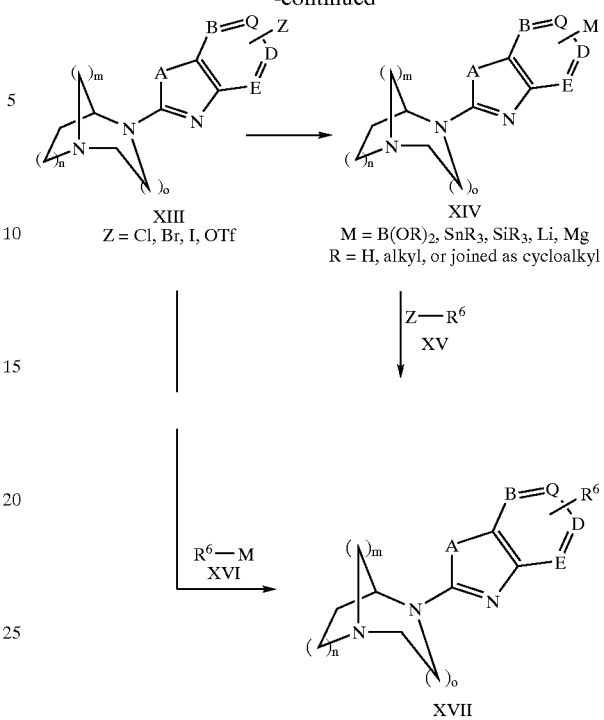

Scheme 4 illustrates an alternative preparation of compounds of the formula I wherein B, Q, D, or E is Cl, Br, I or wherein B, Q, D, or E is optionally substituted with a (C₆–C₁₁)aryl or 5–12 membered heteroaryl (R⁶) group. Referring to Scheme 4, treatment of a compound of the formula XI with a halogenating reagent such as but not limited to Cl₂, Br₂, I₂, N-bromosuccinimide, N-chlorosuccinimide, or N-iodosuccinimide in an inert reaction solvent such as water, acetic acid, methanol, ethanol, tetrhydrofuran, carbon tetrachloride, chloroform, acetonitrile or mixtures thereof in the presence or absence of a base such as potassium acetate, sodium acetate, cesium acetate, sodium carbonate, lithium carbonate, potassium carbonate, cesium carbonate, cesium fluoride n-butyllithium, lithium diisopropyl amide at −78° C. to 100° C.; preferable Br₂ in water and acetic acid with sodium acetate at 25° C. to 100° C. produces a compound of formula XIII where Z is Br. Alternatively, a compound of formula XIII where Z=OTf can be prepared by reaction of a compound of formula XII wherein one of the substituents on B, Q, D, or E is a hydroxy group with trifluoroacetic anhydride, N-phenyltrifluoromethanesulfonimide, or 2-[N,N-bis(trifluoromethylsulfonyl)amino]-5-chloropyridine in the presence of a base such as but not limited to triethylamine, diethylisopropylamine, lithium diisopropyl amide, potassium diisopropyl amide, lithium hexamethyldisilazide, potassium hexamethyldisilazide, pyridine, lutidine, collidine, sodium or potassium hydroxide, sodium or potassium or cesium carbonate, sodium or potassium tert-butoxide, sodium or potassium hydrogen carbonate, sodium or potassium acetate in an inert reaction solvent such as ether, tetrahydrofuran, 1,2-dimethoxyethane, dioxanes, methylene chloride, chloroform, benzene, toluene at −78° C. to 100° C.; preferable N-phenyltrifluoromethanesulfonimide, lithium diisopropyl amide in THF at −78° C. to 25° C.

Referring to Scheme 4, a compound of the formula I wherein B, Q, D, or E is optionally substituted with a ($C_6$–$C_{11}$)aryl or 5–12 membered heteroaryl ($R^6$) group can be prepared from a compound of formula XIII wherein Z is chloro, bromo, iodo or triflate (OTf) by first reacting it with bis(pinacolato)diboron and a palladium catalyst such as palladium (0) tetrakis(triphenylphosphine), palladium (II) acetate, allyl palladium chloride dimer, tris (dibenzylideneacetone)dipalladium (0), tris(dibenzylideneacetone)dipalladium (0) chloroform adduct, palladium (II) chloride or dichloro[1,1'-bis(diphenylphosphino)ferrocene] palladium (II) dichloromethane adduct, preferably dichloro [1,1'-bis(diphenylphosphino)-ferrocene]palladium (II) dichloromethane adduct, in the presence or absence of a phosphine ligand such as 1,1'-bis(diphenylphosphino) ferrocene, triphenylphosphine, tri-o-tolylphosphine, tri-tert-butylphosphine, 1,2-bis(diphenylphosphino)ethane, 1,3-bis (diphenylphosphino)-propane, BINAP, 2-biphenyl dicyclohexylphosphine, 2-biphenyl-di-tert-butylphosphine, 2-(N,N-dimethylamino)-2'-di-tert-butylphosphino-biphenyl or 2-(N,N-dimethylamino)-2'-dicyclohexylphosphinobiphenyl, preferably 1,1'-bis (diphenylphosphino)ferrocene, and in the presence or absence of a base such as potassium acetate, sodium acetate, cesium acetate, sodium carbonate, lithium carbonate, potassium carbonate, cesium carbonate or cesium fluoride, preferably potassium acetate, to yield a compound of the formula XIV wherein the Z group has been replaced with M, wherein M=borane pinacol ester. Generally, this reaction is carried out in a reaction inert solvent such as 1,4-dioxane, acetonitrile, methyl sulfoxide, tetrahydrofuran, ethanol, methanol, 2-propanol, toluene, preferably methyl sulfoxide, at a temperature from about from 0° C. to about 200° C., preferably from about 80° C. to about 120° C.

Other methods of converting a compound of the formula XIII with the Z group mentioned above into a compound of the formula XIV wherein the Z group is replaced with M, wherein M is boronic acid, boronic acid ester or trialkylstannane, are known in the art. For instance, treatment of a compound of the formula XIII, wherein Z is Br or I, with an alkyl lithium reagent such as, but not limited to n-butyl lithium, sec butyl lithium or tert-butyl lithium, in a solvent such as diethyl ether, tetrahydrofuran, 1,2-dimethoxyethane, hexane, toluene, dioxane or a similar reaction inert solvent, at a temperature from about −100° C. to about 25° C. affords the corresponding compound of the formula XIV wherein Z is Li. Treatment of a solution of this material with a suitable boronic ester such as trimethoxyborane, triethoxyborane or triisopropylborane, followed by a standard aqueous work-up with acid will afford the corresponding compound of the formula XIV wherein M is boronic acid.

Alternatively, treating a mixture of a compound of the formula XIII wherein Z is Br or I and a boronic ester with an alkyl lithium reagent, as described above, followed by a standard aqueous work-up with acid will afford the corresponding compound of formula XIV wherein M is boronic acid. Alternatively, treating a compound of the formula XIII wherein Z is Br or I with an alkyl lithium reagent such as, but not limited to n-butyl lithium, sec butyl lithium or tert-butyl lithium, in a solvent such as dieathyl ether, tetrahydrofuran, dimethoxyethane, hexane, toluene, dioxane or a similar reaction inert solvent, at a temperature from about −100° C. to about 25° C. will afford the corresponding compound of the formula XIV wherein M is Li. Treatment of a solution of this material with a suitable trialkylstannyl halide such as, but not limited to trimethylstannyl chloride or bromide or tributylstannyl chloride or bromide, followed by a standard aqueous work-up will afford the corresponding compound of the formula XIV wherein M is trimethyl or tributylstannane.

Referring to Scheme 4, treatment of a compound of the formula XIV wherein M is a boronic acid, boronic ester, or trialkylstannane group, with an aryl or heteroaryl chloride, aryl or heteroaryl bromide, aryl or heteroaryl iodide, or aryl or heteroaryl triflate of the formula XV, preferably an aryl or heteroaryl bromide, with a palladium catalyst such as palladium (0) tetrakis(triphenylphosphine), palladium (II) acetate, allyl palladium chloride dimer, tris (dibenzylideneacetone)dipalladium (0), tris (dibenzylideneacetone)dipalladium (0) chloroform adduct, palladium (II) chloride or dichloro[1,1'-bis (diphenylphosphino)ferrocene]palladium (II) dichloromethane adduct, preferably dichloro[1,1'-bis (diphenylphosphino)-ferrocene]palladium (II) dichloromethane adduct, in the presence or absence of a phosphine ligand such as 1,1'-bis(diphenylphosphino) ferrocene, triphenylphosphine, tri-o-tolylphosphine, tri-tert-butylphosphine, 1,2-bis(diphenylphosphino)ethane, 1,3-bis (diphenylphosphino)-propane, BINAP, 2-biphenyl dicyclohexylphosphine, 2-biphenyl-di-tert-butylphosphine, 2-(N,N-dimethylamino)-2'-di-tert-butylphosphino-biphenyl or 2-(N,N-dimethylamino)-2'-dicyclohexylphosphinobiphenyl, preferably 1,1'-bis (diphenylphosphino)ferrocene, and in the presence or absence of a base such as potassium phosphate, potassium acetate, sodium acetate, cesium acetate, sodium carbonate, lithium carbonate, potassium carbonate, cesium fluoride or cesium carbonate, preferably potassium phosphate, affords a compound of formula XVII. This reaction is typically carried out in a reaction inert solvent such as 1,4-dioxane, acetonitrile, methyl sulfoxide, tetrahydrofuran, ethanol, methanol, 2-propanol, or toluene, preferably 1,4-dioxane, in the presence or absence of from about 1%–about 10% water, preferably about 5% water, at a temperature from about 0° C. to about 200° C., preferably from about 60° C. to about 100° C.

Referring to Scheme 4, alternatively, a compound of the formula Xil can be reacted with a compound of the formula XVI, wherein M is a boronic acid, boronic acid ester, borane pinacol ester or trialkylstannane group, in the presence of a palladium catalyst such as palladium (0) tetrakis (triphenylphosphine), palladium (II) acetate, allyl palladium chloride dimer, tris(dibenzylideneacetone)dipalladium (0), tris(dibenzylideneacetone)dipalladium (0) chloroform adduct, palladium (II) chloride or dichloro[1,1'-bis (diphenylphosphino)ferrocene]palladium (II) dichloromethane adduct, preferably palladium (II) acetate, in the presence or absence of a phosphine ligand such as 1,1'-bis (diphenylphosphino)ferrocene, triphenylphosphine, tri-o-tolylphosphine, tri-tert-butylphosphine, 1,2-bis (diphenylphosphino)ethane, 1,3-bis(diphenylphosphino)-propane, BINAP, 2-biphenyl dicyclohexylphosphine, 2-biphenyl-di-tert-butylphosphine, 2-(N,N-dimethylamino)-2'-di-tert-butylphosphino-biphenyl or 2-(N,N-dimethylamino)-2'-dicyclohexylphosphinobiphenyl, preferably 2-(N,N-dimethylamino)-2'-dicyclohexylphosphinobiphenyl, and in the presence or absence of a base such as potassium phosphate, potassium acetate, sodium acetate, cesium acetate, sodium carbonate, lithium carbonate, potassium carbonate, cesium fluoride or cesium carbonate, preferably cesium fluoride, affords a compound of formula XVII. This reaction is typically carried out in a reaction inert solvent such as 1,4-dioxane, 1,2-dimethoxyethane, acetonitrile, methyl sulfoxide, tetrahydrofuran, ethanol, methanol, 2-propanol, or toluene, preferably 1,2-dimethoxyethane, in the presence or absence of from about 1% to about 10% triethylamine, preferably about 1% triethylamine, at a temperature from about 0° C. to about 200° C., preferably from about 60° C. to about 100° C.

Isolation and purification of the products can be accomplished by standard procedures that are known to a chemist of ordinary skill.

In each of the reactions discussed above, or illustrated in Schemes 1–4, above, pressure is not critical unless otherwise indicated. Pressures from about 0.5 atmospheres to about 5 atmospheres are generally acceptable, with ambient pressure, i.e., about 1 atmosphere, being preferred as a matter of convenience.

The compounds of the formula I and their pharmaceutically acceptable salts (hereafter "the active compounds") can be administered via either the oral, transdermal (e.g., through the use of a patch), intranasal, sublingual, rectal, parenteral or topical routes. Transdermal and oral administration are preferred. These compounds are, most desirably, administered in dosages ranging from about 0.25 mg up to about 1500 mg per day, preferably from about 0.25 to about 300 mg per day in single or divided doses, although variations will necessarily occur depending upon the weight and condition of the subject being treated and the particular route of administration chosen. However, a dosage level that is in the range of about 0.01 mg to about 10 mg per kg of body weight per day is most desirably employed. Variations may nevertheless occur depending upon the weight and condition of the persons being treated and their individual responses to said medicament, as well as on the type of pharmaceutical formulation chosen and the time period and interval during which such administration is carried out. In some instances, dosage levels below the lower limit of the aforesaid range may be more than adequate, while in other cases still larger doses may be employed without causing any harmful side effects, provided that such larger doses are first divided into several small doses for administration throughout the day.

The active compounds can be administered alone or in combination with pharmaceutically acceptable carriers or diluents by any of the several routes previously indicated. More particularly, the active compounds can be administered in a wide variety of different dosage forms, e.g., they may be combined with various pharmaceutically acceptable inert carriers in the form of tablets, capsules, transdermal patches, lozenges, troches, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various non-toxic organic solvents. In addition, oral pharmaceutical compositions can be suitably sweetened and/or flavored. In general, the active compounds are present in such dosage forms at concentration levels ranging from about 5.0% to about 70% by weight.

For oral administration, tablets containing various excipients such as microcrystalline cellulose, sodium citrate, calcium carbonate, dicalcium phosphate and glycine may be employed along with various disintegrants such as starch (preferably corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc can be used for tabletting purposes. Solid compositions of a similar type may also be employed as fillers in gelatin capsules; preferred materials in this connection also include lactose or milk sugar, as well as high molecular weight polyethylene glycols. When aqueous suspensions and/or elixirs are desired for oral administration the active ingredient may be combined with various sweetening or flavoring agents, coloring matter and, if so desired, emulsifying and/or suspending agents, together with such diluents as water, ethanol, propylene glycol, glycerin and various combinations thereof.

For parenteral administration, a solution of an active compound in either sesame or peanut oil or in aqueous propylene glycol can be employed. The aqueous solutions should be suitably buffered (preferably pH greater than 8), if necessary, and the liquid diluent first rendered isotonic. These aqueous solutions are suitable for intravenous injection purposes. The oily solutions are suitable for intraarticular, intramuscular and subcutaneous injection purposes. The preparation of all these solutions under sterile conditions is readily accomplished by standard pharmaceutical techniques well known to those skilled in the art.

It is also possible to administer the active compounds topically and this can be done by way of creams, a patch, jellies, gels, pastes, ointments and the like, in accordance with standard pharmaceutical practice.

The effectiveness of the active compounds in suppressing nicotine binding to specific receptor sites can be determined by the following procedure, which is a modification of the methods of Lippiello, P. M. and Fernandes, K. G. (in "The Binding of L-[$^3$H]Nicotine To A Single Class of High-Affinity Sites in Rat Brain Membranes", *Molecular Pharm.*, 29, 448–54, (1986)) and Anderson, D. J. and Arneric, S. P. (in "Nicotinic Receptor Binding of $^3$H-Cystisine, $^3$H-Nicotine and $^3$H-Methylcarmbamylcholine In Rat Brain", *European J. Pharm.*, 253, 261–67 (1994)). Male Sprague-Dawley rats (200–300 g) from Charles River were housed in groups in hanging stainless steel wire cages and were maintained on a 12 hour light/dark cycle (7 a.m.–7 p.m. light period). They received standard Purina Rat Chow and water ad libitum. The rats were killed by decapitation. Brains were removed immediately following decapitation. Membranes were prepared from brain tissue according to the methods of Lippiello and Fernandez (*Molec. Pharmacol.*, 29, 448–454, (1986)) with some modifications. Whole brains were removed, rinsed with ice-cold buffer, and homogenized at 0° in 10 volumes of buffer (w/v) using a Brinkmann Polytron™ (Brinkmann Instruments Inc., Westbury, N.Y.), setting 6, for 30 seconds. The buffer consisted of 50 mM Tris HCl at a pH of 7.5 at room temperature. The homogenate was sedimented by centrifugation (10 minutes; 50,000×g; 0° to 4° C.). The supernatant was poured off and the membranes were gently resuspended with the Polytron and centrifuged again (10 minutes; 50,000×g; 0° C. to 4° C.). After the second centrifugation, the membranes were resuspended in assay buffer at a concentration of 1.0 g/100 mL. The composition of the standard assay buffer was 50 mM Tris HCl, 120 mM NaCl, 5 mM KCl, 2 mM MgCl$_2$, 2 mM CaCl$_2$ and had a pH of 7.4 at room temperature.

Routine assays were performed in borosilicate glass test tubes. The assay mixture typically consisted of 0.9 mg of membrane protein in a final incubation volume of 1.0 mL. Three sets of tubes were prepared wherein the tubes in each set contained 50 μL of vehicle, blank, or test compound solution, respectively. To each tube was added 200 μL of [$^3$H]-nicotine in assay buffer followed by 750 μL of the membrane suspension. The final concentration of nicotine in each tube was 0.9 nM. The final concentration of cytisine in the blank was 1 μM. The vehicle consisted of deionized water containing 30 μL of 1 N acetic acid per 50 mL of water. The test compounds and cytisine were dissolved in vehicle. Assays were initiated by vortexing after addition of the membrane suspension to the tube. The samples were incubated at 0° to 4° C. in an iced shaking water bath. Incubations were terminated by rapid filtration under vacuum through Whatman GF/B™ glass fiber filters (Brandel Biomedical Research & Development Laboratories, Inc., Gaithersburg, Md.) using a Brandel™ multi-manifold tissue harvester (Brandel Biomedical Research & Development Laboratories, Inc., Gaithersburg, Md.). Following the initial filtration of the assay mixture, filters were washed two times with ice-cold assay buffer (5 ml each). The filters were then placed in counting vials and mixed vigorously with 20 ml of Ready Safe™ (Beckman, Fullerton, Calif.) before quantification of radioactivity. Samples were counted in a LKB Wallac Rackbeta™ liquid scintillation counter (Wallac Inc., Gaithersburg, Md.) at 40–50% efficiency. All determinations were in triplicate.

Calculations: Specific binding (C) to the membrane is the difference between total binding in the samples containing vehicle only and membrane (A) and non-specific binding in the samples containing the membrane and cytisine (B), i.e., Specific binding=$(C)=(A)-(B)$.

Specific binding in the presence of the test compound (E) is the difference between the total binding in the presence of the test compound (D) and non-specific binding (B), i.e., $(E)=(D)-(B)$.

% Inhibition=$(1-((E)/(C)))$ times 100.

The compounds of the invention that were tested in the above assay exhibited $IC_{50}$ values of less than 100 μM.

[$^{125}$I]-Bungarotoxin binding to nicotinic receptors in $GH_4Cl$ cells: Membrane preparations were made for nicotinic receptors expressed in $GH_4Cl$ cell line. Briefly, one gram of cells by wet weight were homogenized with a polytron in 25 mls of buffer containing 20 mM Hepes, 118 mM NaCl, 4.5 mM KCl, 2.5 mM $CaCl_2$, 1.2 mM $MgSO_4$, pH 7.5. The homogenate was centrifuged at 40,000×g for 10 min at 4° C., the resulting pellet was homogenized and centrifuged again as described above. The final pellet was resuspended in 20 mls of the same buffer. Radioligand binding was carried out with [$^{125}$I] alpha-bungarotoxin from New England Nuclear, specific activity about 16 uCi/ug, used at 0.4 nM final concentration in a 96 well microtiter plate. The plates were incubated at 37° C. for 2 hours with 25 μl drugs or vehicle for total binding, 100 μl [$^{125}$I] Bungarotoxin and 125 μl tissue preparation. Nonspecific binding was determined in the presence of methyllycaconitine at 1 μM final concentration. The reaction was terminated by filtration using 0.5% Polyethylene imine treated Whatman GF/B™ glass fiberfilters (Brandel Biomedical Research & Development Laboratories, Inc., Gaithersburg, Md.) on a Skatron cell harvester (Molecular Devices Corporation, Sunnyvale, Calif.) with ice-cold buffer, filters were dried overnight, and counted on a Beta plate counter using Betaplate Scint. (Wallac Inc., Gaithersburg, Md.). Data are expressed as IC50's (concentration that inhibits 50% of the specific binding) or as an apparent Ki, IC50/1+ [L]/KD. [L]=ligand concentration, KD=affinity constant for [$^{125}$I] ligand determined in separate experiment.

The compounds of the invention that were tested in the above assay exhibited $IC_{50}$ values of less than 10 μM.

[$^{125}$I]-Bungarotoxin binding to alpha1 nicotinic receptors in Torpedo electroplax membranes: Frozen Torpedo electroplax membranes (100 μl) were resuspended in 213 mls of buffer containing 20 mM Hepes, 118 mM NaCl, 4.5 mM KCl, 2.5 mM $CaCl_2$, 1.2 mM $MgSO_4$, pH 7.5 with 2 mg/ml BSA. Radioligand binding was carried out with [$^{125}$I] alpha-bungarotoxin from New England Nuclear, specific activity about 16 uCi/ug, used at 0.4 nM final concentration in a 96 well microtiter plate. The plates were incubated at 37° C. for 3 hours with 25 μl drugs or vehicle for total binding, 100 μl [$^{125}$I] Bungarotoxin and 125 μl tissue preparation. Nonspecific binding was determined in the presence of alpha-bungarotoxin at 1 μM final concentration. The reaction was terminated by filtration using 0.5% Polyethylene imine treated GF/B filters on a Brandel cell harvester with ice-cold buffer, filters were dried overnight, and counted on a Beta plate counter using Betaplate Scint. Data are expressed as IC50's (concentration that inhibits 50% of the specific binding) or as an apparent Ki, IC50/1 +[L]/KD. [L]=ligand concentration, KD=affinity constant for [$^{125}$I] ligand determined in separate experiment.

The compounds of the invention that were tested in the above assay exhibited $IC_{50}$ values of less than 100 μM.

5-$HT_3$ Receptor Binding in NG-108 Cells Using 3H-LY278584: NG-108 cells endogenously express 5-$HT_3$ receptors. Cells are grown in DMEM containing 10% fetal bovine serum supplemented with L-glutamine (1:100). Cells are grown to confluence and harvested by removing the media, rinsing the flasks with phosphate buffered saline (PBS) and then allowed to sit for a 2–3 minutes with PBS containing 5 mM EDTA. Cells are dislodged and poured into a centrifuge tube. Flasks are rinsed with PBS and added to centrifuge tube. The cells are centrifuged for ten minutes at 40,000×g (20,000 rpm in Sorvall SS34 rotor(Kendro Laboratory Products, Newtown, Conn.)). The supernatant is discarded (into chlorox) and at this point the remaining pellet is weighed and can be stored frozen (−80 degrees C.) until used in the binding assay. Pellets (fresh or frozen −250 mgs per 96 well plate) are homogenized in 50 mM Tris HCl buffer containing 2 mM $MgCl_2$ (pH 7.4) using a Polytron homogenizer (setting 15,000 rpm) for ten seconds. The homogenate is centrifuged for ten minutes at 40,000×g. The supernatant is discarded and the pellet resuspended with the Polytron in fresh ice-cold 50 mM Tris HCl containing 2 mM $MgCl_2$ (pH 7.4) buffer and centrifuged again. The final pellet is resuspended in assay buffer (50 mM Tris HCl buffer (pH 7.4 at 37° C. degrees) containing 154 mM NaCl,) for a final tissue concentration of 12.5 mg per mL buffer (1.25× final concentration). Incubations were initiated by the addition of tissue homogenate to 96 well polypropylene plates containing test compounds that have been diluted in 10% DMSO/50 mM Tris buffer and radioligand (1 nM final concentration of 3H-LY278584). Nonspecific binding was determined using a saturating concentration of a known potent 5-$HT_3$ antagonist (10 μM ICS-205930). After an hour incubation at 37° C. in a water bath, the incubation is ended by rapid filtration under vacuum through a fire-treated Whatman. GF/B glass fiber filter (presoaked in 0.5% Polyethylene imine for two hours and dried) using a 96 well Skatron Harvester (3 sec pre-wet; 20 seconds wash; 15 seconds dry). Filters are dried overnight and then placed into Wallac sample bags with 10 mLs BetaScint. Radioactivity is quantified by liquid scintillation counting using a BetaPlate counter (Wallac, Gaithersburg, Md.). The percent inhibition of specific binding is calculated for each concentration of test compound. An IC50 value (the concentration which inhibits 50% of the specific binding) is determined by linear regression of the concentration-response data (log concentration vs. logit percent values). Ki values are calculated according to Cheng & Prusoff−Ki=IC50/(1+(L/Kd)), where L is the concentration of the radioligand used in the experiment and the Kd value is the dissociation constant for the radioligand determined in separate saturation experiments.

The compounds of the invention that were tested in the above assay exhibited $IC_{50}$ values of less than 100 µM.

The following experimental examples illustrate but do not limit the present invention. In the examples, commercial reagents were used without further purification. Purification by chromatography was done on prepacked silica columns from Biotage (Dyax Corp, Biotage Division, Charlottesville, Va.). Melting points (mp) were obtained using a Mettler Toledo FP62 melting point apparatus (Mettler-Toledo, Inc., Worthington, Ohio) with a temperature ramp rate of 10° C./min and are uncorrected. Proton nuclear magnetic resonance ($^1$H NMR) spectra were recorded in deuterated solvents on a Varian INOVA400 (400 MHz) spectrometer (Varian NMR Systems, Palo Alto, Calif.). Chemical shifts are reported in parts per million (ppm, δ) relative to $Me_4Si$ (δ 0.00). Proton NMR splitting patterns are designated as singlet (s), doublet (d),-triplet (t), quartet (q), quintet (quin), sextet (sex), septet (sep), multiplet (m) apparent (ap) and broad (br). Coupling constants are reported in hertz (Hz). Carbon-13 nuclear magnetic resonance ($^{13}$C NMR) spectra were recorded on a Varian INOVA400 (100 MHz). Chemical shifts are reported in ppm (δ) relative to the central line of the 1:1:1 triplet of deuterochloroform (δ 77.00), the center line of deuteromethanol (δ 49.0) or deuterodimethylsulfoxide (δ 39.7). The number of carbon resonance's reported may not match the actual number of carbons in some molecules due to magnetically and chemically equivalent carbons and may exceed the number of actual carbons due to conformational isomers. Mass spectra (MS) were obtained using a Waters ZMD mass spectrometer using flow injection atmospheric pressure chemical ionization (APCI) (Waters Corporation, Milford, Mass.). Gas chromatography with mass detection (GCMS) were obtained using a Hewlett Packard HP 6890 series GC system with a HP 5973 mass selective detector and a HP-1 (crosslinked methyl siloxane) column (Agilent Technologies, Wilmington, Del.). HPLC spectra were recorded on a Hewlett Packard 1100 series HPLC system with a Zorbax SB-C8, 5 µm, 4.6×150 mm column (Agilent Technologies, Wilmington, Del.) at 25° C. using gradient elution. Solvent A is water, Solvent B is acetonitrile, Solvent C is 1% trifluoroacetic acid in water. A linear gradient over four minutes was used starting at 80% A, 10% B, 10% C and ending at 0% A, 90% B, 10% C. The eluent remained at 0% A, 90% B, 10% C for three minutes. A linear gradient over one minute was used to return the eluent to 80% A, 10% B, 10% C and it was held at this until the run time equaled ten minutes. Room temperature (RT) refers to 20–25° C. The abbreviations "h" and "hrs" refer to "hours". 1,4-Diaza-bicyclo[3.2.2]nonane was prepared via slight modifications of the published procedure: see, Rubstov, M. V.; Mikhlina, E. E.; Vorob'eva, V. Ya.; Yanina, A. *Zh. Obshch. Khim.* 1964, V34, 2222–2226.

EXAMPLE 1

4-BENZOOXAZOL-2-YL-1,4-DIAZA-BICYCLO [3.2.2]NONANE

2-Chlorobenzoxazole (Aldrich, 99 µL, 0.87 mmol) was added to a solution of 1,4-diazabicyclo[3.2.2]nonane (100 mg, 0.79 mmol) in methanol (2.65 mL) at 0° C. The reaction mixture was allowed to slowly warm to RT. After a period of 16 h $iPr_2NEt$ (138 µL, 0.79 mmol) was added and the mixture was stirred at RT for 4.5 h at which time it was diluted with $CHCl_3$ and $NaHCO_3$. The layers were partitioned and the aqueous layer was extracted with $CHCl_3$ (×3). The combined organic layers were washed with $H_2O$ and brine, dried ($Na_2SO_4$), filtered and concentrated. The crude residue was purified by chromatography (Biotage, 12L) eluting with 4% MeOH in $CHCl_3$ containing 20 drops of $NH_4OH$ per liter of eluent to afford 67 mg (35%) of the title compound as a yellow oil: $^1$H NMR ($CDCl_3$, 400 MHz) δ 7.30 (d, 1H, J=7.5 Hz), 7.19 (d, 1H, J=7.9 Hz), 7.10 (t, 1H, J=7.5 Hz), 6.94 (t, 1H, J=7.9 Hz), 4.46 (s, 1H), 3.87, (t, 2H, J=5.8 Hz), 3.12–2.92 (m, 6H), 2.15–2.05 (m, 2H), 1.79–1.70 (m, 2H); $^{13}$C NMR ($CDCl_3$, 100 MHz) δ 161.8, 148.9, 143.7, 124.1, 120.3, 116.1, 108.7, 57.3, 50.3, 46.5, 44.4, 27.1; MS (Cl) m/z 244.3 (M+1). The hydrochloride salt was prepared by dissolving the title compound in iPrOH and adding 0.1 mL of 6 M hydrochloric acid.

EXAMPLE 2

4-BENZOTHIAZOL-2-YL-1,4-DIAZA-BICYCLO [3.2.2]NONANE

2-Chlorobenzothiazole (Aldrich, 109 µL, 0.841 mmol) was added to a solution of 1,4-diazabicyclo[3.2.2]nonane (57%, 169 mg, 0.765 mmol), $Et_3N$ (213 µL, 1.53 mmol) in DMF (2.5 mL). The reaction mixture was heated at 100° C. for 2 h. The mixture was allowed to cool to RT, diluted with EtOAc and $H_2O$ and the layers were partitioned. The aqueous layer was extracted with EtOAc (3×) and the combined organic extracts were washed successively with $H_2O$ and brine and then dried ($Na_2SO_4$), filtered and concentrated. The crude residue was purified by chromatography (Biotage, 12L) eluting with 5% MeOH in $CHCl_3$ to afford 68 mg (34%) of the title compound as a yellow oil: $^1$H NMR ($CDCl_3$, 400 MHz) δ 7.58 (d, 1H, J=7.9 Hz), 7.57 (d, 1H, J=7.9 Hz), 7.27 (t, 1H, J=8.3 Hz), 7.04 (td, 1H, J=7.9, 1.2 Hz), 4.31 (s, 1H), 3.92 (t, 2H, J=5.8 Hz), 3.19–2.98 (m, 6H), 2.25–2.16 (m, 2H), 1.84–1.77 (m, 2H), MS (Cl) m/z 260.2 (M+1). The hydrochloride salt was prepared by dissolving the title compound in iPrOH and adding 0.1 mL of 6 M hydrochloric acid.

The 2-mercaptobenzoxazoles were prepared by two different methods and the general procedures are described in the literature, see: Sato, Y.; Yamada, M.; Yoshida, S.; Soneda, T.; Ishikawa, M.; Nizato, T.; Suzuki, K.; Konno, F. *J. Med. Chem.* 1998, 41, 3015–3021 and Van Allan, J. A.; Deacon, B. D. *Organic Syntheses*; Wiley: New York, 1963; Collect. Vol. IV, pp 569–70.

EXAMPLE 3

5-PHENYL-3H-BENZOOXAZOLE-2-THIONE

Carbon disulfide (7.7 mL) was added to a mixture of 2-amino-4-phenylphenol (1.0 g, 5.4 mmol), potassium hydroxide (0.36 g, 6.5 mmol) and ethanol (11.7 mL). The flask was fitted with a reflux condenser and the resulting mixture was placed in an oil bath at 60° C. for 16 h. After cooling to RT, the mixture was concentrated and ethyl acetate (20 mL) and 1 M hydrochloric acid (10 mL) were added to the residue. The layers were partitioned and the organic layer was washed successively with 1 M HCl, water and brine. The organic layer was dried ($Na_2SO_4$), filtered and concentrated to afford 1.20 g (98%) which was used without further purification: $^1$H NMR (d6-DMSO, 400 MHz) δ 13.98 (s, 1H), 7.64–7.62 (m, 2H), 7.58–7.49 (m, 2H), 7.46–7.42 (m, 2H), 7.39–7.33 (m, 2H); $^{13}$C (d6-DMSO, 400 MHz) δ 181.2, 148.2, 140.1, 138.5, 132.7, 129.7, 128.3, 127.7, 123.4, 111.0, 109.1; MS (Cl) m/z 228.1 (M+1); HPLC retention time=3.09 min.

EXAMPLE 4

2-AMINO-4-BROMOPHENOL

A solution of KOH (5.14 g, 91.7 mmol) in water (33 mL) was added to 4-bromo-2-nitrophenol (Aldrich, 1.00 g, 4.59 mmol). Sodium hydrosulfite (7.98 g, 45.9 mmol) was added in one portion. The mixture was stirred at RT for 30 min. and poured into ethyl acetate (25 mL). The layers were partitioned and the aqueous layer was extracted with ethyl acetate (4×25 mL). The combined organic layers were dried ($Na_2SO_4$), filtered and concentrated to give 488 mg (56%) of the title compound which was used without further purification: $^1$H NMR ($CDCl_3$, 400 MHz) δ 6.77 (d, 1H, J=2.1 Hz), 6.65 (dd, 1H, J=8.3, 2.5 Hz), 6.52 (d, 1H, J=8.3 Hz); $^{13}$C NMR ($CDCl_3$, 100 MHz) δ 144.0, 136.6, 121.7, 118.7, 116.2, 112.1; MS (CI) m/z 188.0 (M+1); HPLC retention time=1.10 min.

EXAMPLE 5

5-BROMO-3H-BENZOOXAZOLE-2-THIONE

Potassium ethyl xanthate (416 mg, 2.60 mmol) was added to a solution of 2-amino-4-bromophenol (244 mg, 1.30 mmol) in EtOH (3.24 mL). The reaction mixture was heated at reflux for 4 h. Upon cooling to RT the mixture was concentrated and the resulting residue was dissolved in water. Acetic acid was added until pH=5 and a white solid precipitated from the solution. The solid was filtered, washed with water and dried to afford 270 mg (90%) of a tan powder which was used without further purification: $^1$H NMR (d6-DMSO, 400 MHz) δ 14.02 (s, 1H), 7.47–7.38 (m, 3H); $^{13}$C (d6-DMSO, 400 MHz) δ 181.4, 148.1, 133.7, 127.1, 117.8, 118.8, 112.2; MS (CI) m/z 229.8 (M−1); HPLC retention time=4.34 min.

The 2-chlorobenzoxazole compounds were prepared by the general procedures described in the literature, see: Lok, R.; Leone, R. E.; Williams, A. J. *J. Org. Chem.* 1996, 61, 3289–3297.

EXAMPLE 6

2-CHLORO-5-PHENYLBENZOXAZOLE

5-Phenyl-3H-benzooxazole-2-thione (227 mg, 1.0 mmol) was dissolved in phosphorus oxychloride (1.6 mL). Phosphorus pentachloride (208 mg, 1.0 mmol) was added and the mixture was placed in an oil bath at 100° C. for 3 h. The mixture was allowed to cool to RT and concentrated. The crude residue was concentrated from $CH_2Cl_2$ (3×). The crude reaction product was triturated with hexanes (40 mL), and the resulting solids were collected by filtration. The solids were washed with hexanes (20 mL×3) and dried to afford 1.47 g (73%) of the title compound: $^1$H NMR ($CDCl_3$, 400 MHz) δ 7.86 (d, 1H, J=1.3 Hz), 7.60–7.56 (m, 3H), 7.55–7.52 (m, 1H), 7.49–7.44 (m, 2H), 7.40–7.36 (m, 1H); $^{13}$C NMR ($CDCl_3$, 100 MHz) δ 151.6, 151.4, 141.9, 140.7, 139.3, 129.2, 127.8, 127.7, 125.2, 118.4, 110.7; MS (CI) m/z 230.1 (M+1); HPLC retention time=5.41 min.

The 2-methylthiobenzoxazole compounds were prepared by the general procedures described in the literature, see: Yamato, M.; Takeuchi, Y.; Hashigaki, K.; Hirota, T. *Chem. Pharm. Bull.* 1983, 31, 733–736.

EXAMPLE 7

5-BROMO-2-METHYLSULFANYL-BENZOOXAZOLE

5-Bromo-3H-benzooxazole-2-thione (530 mg, 2.30 mmol) was dissolved in DMF (5.75 mL). Potassium carbonate (318 mg, 2.30 mmol) and iodomethane (172 μL, 2.76 mmol) were added and the reaction mixture was allowed to stir at RT for 3.5 h. The mixture was diluted with water (10 mL) and extracted with ethyl acetate (4×10 mL): The combined organic extracts were washed with water (3×10 mL), brine (10 mL) and dried ($Na_2SO_4$), filtered and concentrated to afford 538 mg (96%) of the title compound as a dark brown solid:

$^1$H NMR ($CDCl_3$, 400 MHz) δ 7.72 (d, 1H, J=2.1 Hz), 7.36–7.26 (m, 2H), 2.75 (s, 3H); $^{13}$C NMR ($CDCl_3$, 100 MHz) δ 167.6, 151.2, 143.8, 126.9, 121.6, 117.3, 111.2, 14.8; MS (CI) m/z 244.0 (M+1); HPLC retention time=5.10 min.

EXAMPLE 8

4-(5-PHENYL-BENZOOXAZOL-2-YL)-1,4-DIAZA-BICYCLO[3.2.2]NONANE 1,4-Diazabicyclo[3.2.2]nonane (504 mg, 4.0 mmol) was added to a mixture of 2-chloro-5-phenylbenzoxazole (919 mg, 4.0 mmol), sodium tert-butoxide (423 mg, 4.4 mmol) and toluene (4 mL) at RT. The mixture was stirred at RT for 16 h and water (10 mL) and ethyl acetate (10 mL) were added. The layers were partitioned and the aqueous layer was extracted with ethyl acetate (3×10 mL). The combined organic layers were dried ($Na_2SO_4$), filtered and concentrated and the residue was purified by chromatography (Biotage, 40S) eluting with 4% MeOH in $CHCl_3$ with 20 drops of $NH_4OH$ per liter of eluent to afford 540 mg (42%) of the title compound as an oil: $^1$H NMR ($CDCl_3$, 400 MHz) δ 7.60–7.56 (m, 3H), 7.42 (t, 2H, J=7.7 Hz), 7.33–7.20 (m, 3H), 4.51 (s, 1H), 3.92 (t, 2H, J=5.8 Hz), 3.17–2.97 (m, 6H), 2.20–2.07 (m, 2H), 1.84–1.75 (m, 2H); $^{13}$C NMR ($CDCl_3$, 100 MHz) δ 162.2, 148.6, 144.3, 141.9, 137.9, 129.0, 127.5, 127.1, 119.8, 114.8, 108.8, 57.3, 50.4, 46.5, 44.4, 27.0; MS (CI) m/z 320.1 (M+1). The hydrochloride salt was prepared by diluting the title compound in ethyl acetate and adding a 2.5 N HCl in ethyl acetate solution: mp>300° C.

EXAMPLE 9

4-(5-BROMO-BENZOOXAZOL-2-YL)-1,4-DIAZA-BICYCLO[3.2.2]NONANE 1,4-Diazabicyclo[3.2.2]nonane (57%, 731 mg, 3.31 mmol) was added to a solution of 5-bromo-2-methylsulfanyl-benzooxazole (538 mg, 2.20 mmol) in iPrOH (4.4 mL). The mixture was placed in an oil bath at 90° C. and the solvent was evaporated. The mixture was allowed to stir neat at 90° C. for 18 h. Upon cooling to RT the mixture was purified by chromatography (Biotage, 25M) eluting with 4% MeOH in $CHCl_3$ with 20 drops of $NH_4OH$ per liter of eluent to afford 392 mg (55%) of the title compound as an oil: $^1$H NMR ($CDCl_3$, 400 MHz) δ 7.40 (t, 1H, J=1.2 Hz), 7.05 (d, 2H, J=1.2 Hz), 4.46–4.43 (m, 1H), 3.87 (t, 2H, J=5.8 Hz), 3.14–2.93 (m, 6H), 2.13–2.06 (m, 2H), 1.81–1.73 (m, 2H); $^{13}$C NMR ($CDCl_3$, 100 MHz) δ 162.3, 148.0, 145.6, 122.9, 119.0, 116.8, 109.8, 57.2, 50.5, 46.5, 44.4, 27.0; MS (CI) m/z 322.0 (M+1); HPLC retention time=3.36 min. The hydrochloride salt was prepared by diluting in ethyl acetate and adding a solution of 2.5 N HCl in ethyl acetate: mp>300° C.

EXAMPLE 10

3H-1-OXA-3-AZA-CYCLOPENTA[B] NAPHTHALENE-2-THIONE

The title compound was prepared from 3-amino-2-napthol (Aldrich) by the procedure described in Example 3 in 93% yield: $^1$H NMR (d6-DMSO, 400 MHz) δ 7.99–7.92 (m, 3H), 7.64 (s, 1H), 7.48–7.42 (m, 2H); $^{13}$C (d6-DMSO, 100 MHz) δ 182.3, 148.1, 131.7, 131.6, 130.6, 128.7, 128.4, 126.2, 125.9, 106.9, 106.4; MS (CI) m/z 202.1 (M+1); HPLC retention time=4.46 min.

EXAMPLE 11

2-CHLORO-1-OXA-3-AZA-CYCLOPENTA[B] NAPHTHALENE

The title compound was prepared from 3H-1-oxa-3-aza-cyclopenta[b]naphthalene-2-thione by the procedure described in Example 6 in 22% yield: $^1$H NMR (CDCl$_3$, 400 MHz) δ 8.08 (s, 1H), 7.97–7.95 (m, 1H), 7.92–7.90 (m, 1H), 7.84 (s, 1H), 7.54–7.47 (m, 2H); $^{13}$C NMR (CDCl$_3$, 100 MHz) δ 153.7, 150.4, 140.7, 131.6, 131.5, 128.8, 128.2, 126.3, 125.5, 117.5, 106.7; MS (CI) m/z 204.1 (M+1); HPLC retention time=5.17 min.

EXAMPLE 12

2-(1,4-DIAZA-BICYCLO[3.2.2]NON-4-YL)-1-OXA-3-AZA-CYCLOPENTA[B]NAPHTHALENE

The title compound was prepared from 2-chloro-1-oxa-3-aza-cyclopenta[b]naphthalene by the procedure described in Example 8 in 48% yield: $^1$H NMR (CDCl$_3$, 400 MHz) δ 7.85–7.80 (m, 2H), 7.65 (s, 1H), 7.57 (s, 1H), 7.40–7.32 (m, 2H), 4.59–4.58 (m, 1H), 3.97 (t, 2H, J=5.8 Hz), 3.20–3.12 (m, 4H), 3.10–3.00 (m, 2H), 2.21–2.14 (m, 2H), 1.88–1.79 (m, 2H); $^{13}$C NMR (CDCl$_3$, 100 MHz) δ 162.8, 149.2, 144.1, 132.1, 129.5, 127.8, 127.7, 124.5, 123.8, 111.7, 104.6, 57.2, 50.6, 46.5, 44.4, 27.0; MS (CI) m/z 294.2 (M+1); HPLC retention time=3.33 min. The hydrochloride salt was prepared by diluting in ethyl acetate and adding a solution of 2.5 N HCl in ethyl acetate: mp>300° C.

EXAMPLE 13

1H-3-OXA-1-AZA-CYCLOPENTA[A] NAPHTHALENE-2-THIONE

The title compound was prepared from 1-amino-2-naphthol by the procedure described in Example 3 in 98% yield: $^1$H NMR (d4-MeOH, 400 MHz) δ 7.93 (d, 1H, J=8.3 Hz), 7.87 (d, 1H, J=7.9 Hz), 7.65 (d, 1H, J=8.7 Hz), 7.56 (t, 1H, J=8.3 Hz), 7.49–7.43 (m, 2H); MS (CI) m/z 202.1 (M+1).

EXAMPLE 14

2-CHLORO-3-OXA-1-AZA-CYCLOPENTA[A] NAPHTHALENE

The title compound was prepared from 3H-1-oxa-3-aza-cyclopenta[b]naphthalene-2-thione by the procedure described in Example 6 in 77% yield: $^1$H NMR (CDCl$_3$, 400 MHz) δ 8.41 (dd, 1H, J=8.3, 0.8 Hz), 7.94 (d, 1H, J=7.9 Hz), 7.79 (d, 1H, J=9.1 Hz), 7.68–7.53 (m, 3H); $^{13}$C NMR (CDCl$_3$, 100 MHz) δ 149.3, 149.2, 136.9, 131.3, 128.8, 127.7, 126.7, 126.1, 126.0, 122.2, 110.4; MS (CI) m/z 204.1 (M+1).

EXAMPLE 15

2-(1,4-DIAZA-BICYCLO[3.2.2]NON-4-YL)-3-OXA-1-AZA-CYCLOPENTA[A]NAPHTHALENE

The title compound was prepared from 2-chloro-3-oxa-1-aza-cyclopenta[a]naphthalene by the procedure described in Example 8 in 33% yield: $^1$H NMR (CDCl$_3$, 400 MHz) δ 8.33 (d, 1H, J=8.3 Hz), 7.87 (d, 1H, J=8.3 Hz), 7.53–7.40 (m, 4H), 4.60 (s, 1H), 4.01 (t, 2H, J=5.4 Hz), 3.19–3.00 (m, 6H), 2.25–2.15 (m, 2H), 1.88–1.80 (m, 2H); $^{13}$C NMR (CDCl$_3$, 100 MHz) δ 161.9, 145.0, 138.8, 131.3, 128.6, 125.8, 125.0, 124.7, 122.4, 120.5, 109.9, 57.3, 50.2, 46.6, 44.4, 27.1; MS (CI) m/z 294.2 (M+1). The hydrochloride salt was prepared by diluting in ethyl acetate and adding a solution of 2.5 N HCl in ethyl acetate: mp=167.2° C.

EXAMPLE 16

6-PHENYL-3H-BENZOOXAZOLE-2-THIONE

The title compound was prepared from 2-amino-5-phenylphenol (*J. Am. Chem. Soc.* 1993, 115, 9453) by the procedure described in Example 3 in 72% yield: $^1$H NMR (d6-DMSO, 400 MHz) δ 7.79 (s, 1H), 7.64 (d, 2H, J=7.9 Hz), 7.55 (d, 1H, J=8.3 Hz), 7.43 (t, 2H, J=7.5 Hz), 7.34 (d, 1H, J=7.1 Hz), 7.27 (d, 1H, J=8.3 Hz); $^{13}$C (d6-DMSO, 100 MHz) δ 181.0, 149.6, 139.9, 137.1, 131.3, 129.7, 128.3, 127.5, 124.5, 111.3, 108.9; MS (CI) m/z 226.0 (M−1); HPLC retention time=4.60 min.

EXAMPLE 17

2-CHLORO-4-PHENYLBENZOXAZOLE

The title compound was prepared from 6-phenyl-3H-benzooxazole-2-thione by the procedure described in Example 6 in 94% yield: mp=85.8° C.; $^1$H NMR (CDCl$_3$, 400 MHz) δ 7.72–7.68 (m, 2H), 7.61–7.58 (m, 3H), 7.49–7.45 (m, 2H), 7.41–7.37 (m, 1H); $^{13}$C NMR (CDCl$_3$, 100 MHz) δ 152.5, 151.3, 140.6, 140.5, 139.7, 129.2, 128.0, 127.7, 124.8, 119.9, 109.1; MS (CI) m/z 230.1 (M+1); HPLC retention time=5.41 min.

EXAMPLE 18

4-(6-PHENYL-BENZOOXAZOL-2-YL)-1,4-DIAZA-BICYCLO[3.2.2]NONANE

The title compound was prepared from 2-chloro-4-phenylbenzoxazole by the procedure described in Example 8 in 33% yield: $^1$H NMR (CDCl$_3$, 400 MHz) δ 7.58 (d, 2H, J=7.0 Hz), 7.48 (d, 1H, J=1.2 Hz), 7.44–7.36 (m, 3H), 7.30 (t, 2H, J=7.5 Hz), 4.54–4.52 (m, 1H), 3.94 (t, 2H, J=5.8 Hz), 3.19–3.11 (m, 4H), 3.05–2.98 (m, 2H), 2.20–2.12 (m, 2H), 1.86–1.77 (m, 2H); $^{13}$C NMR (CDCl$_3$, 100 MHz) δ 162.1, 149.6, 143.3, 141.6, 134.2, 129.0, 127.2, 126.9, 123.5, 116.0, 107.5, 57.3, 50.5, 46.6, 44.4, 27.1; MS (CI) m/z 320.1 (M+1); HPLC retention time=3.55 min. The hydrochloride salt was prepared by diluting in ethyl acetate and adding a 2.5 N HCl solution in ethyl acetate: mp=281.3° C.

EXAMPLE 19

4-(5-CHLORO-BENZOOXAZOL-2-YL)-1,4-DIAZA-BICYCLO[3.2.2]NONANE

The title compound was prepared from 5-chloro-2-methylsulfanyl-benzooxazole (*Chem. Pharm. Bull.* 1983, 31, 733) by the procedure described in Example 9 in 40% yield: $^1$H NMR (CDCl$_3$, 400 MHz) δ 7.25 (d, 1H, J=2.1 Hz), 7.09 (d, 1H, J=8.3 Hz), 6.91 (dd, 1H), J=8.3, 2.1 Hz), 4.49–4.47 (m, 1H), 3.90 (t, 2H, J=5.8 Hz), 3.20–3.12 (m, 4H), 3.07–2.99 (m, 2H), 2.17–2.09 (m, 2H), 1.85–1.77 (m, 2H); $^{13}$C NMR (CDCl$_3$, 100 MHz) δ 162.4, 147.5, 145.0, 129.4, 120.2, 116.2, 109.3, 57.0, 50.4, 46.3, 44.0, 26.7; MS (CI) m/z 278.1 (M+1); HPLC retention time=3.23 min. The hydrochloride salt was prepared by diluting in ethyl acetate and adding a 2.5 N HCl solution in ethyl acetate: mp>300° C.

EXAMPLE 20

4-(5-FLUORO-BENZOOXAZOL-2-YL)-1,4-DIAZA-BICYCLO[3.2.2]NONANE

The title compound was prepared from 5-fluoro-2-methylsulfanyl-benzooxazole (prepared from 2-amino-4-fluorophenol by the methods described in Example 5 and Example 7) by the procedure described in Example 9 in 15% yield: $^1$H NMR (CDCl$_3$, 400 MHz) δ 7.12 (dd, 1H, J=8.7, 4.6 Hz), 7.01 (dd, 1H, J=9.1, 2.5 Hz), 6.70–6.65 (m, 1H), 4.54–4.51 (m, 1H), 3.94 (t, 2H, J=5.8 Hz), 3.24–3.17 (m, 4H), 3.11–3.03 (m, 2H), 2.21–2.14 (m, 2H), 1.90–1.82 (m, 2H); MS (Cl) m/z 262.1 (M+1); HPLC retention time=3.08 min. The hydrochloride salt was prepared by diluting in ethyl acetate and adding a 2.5 N HCl solution in ethyl acetate: mp>300° C.

EXAMPLE 21

4-(6-NITRO-BENZOOXAZOL-2-YL)-1,4-DIAZA-BICYCLO[3.2.2]NONANE

The title compound was prepared from 2-methylsulfanyl-6-nitro-benzooxazole (prepared from 2-amino-5-nitrophenol by the methods described in Example 5 and Example 7) by the procedure described in Example 9 in 89% yield: $^1$H NMR (CDCl$_3$, 400 MHz) δ 8.11 (dd, 1H, J=8.7, 2.1 Hz), 8.05 (d, 1H, J=2.1 Hz), 7.24 (d, 1H, J=8.7 Hz), 4.51 (s, 1H), 3.94 (t, 2H, J=5.8 Hz), 3.18–3.10 (m, 4H), 3.04–2.96 (m, 2H), 2.15–2.09 (m, 2H), 1.87–1.78 (m, 2H); $^{13}$C NMR (CDCl$_3$, 100 MHz) δ 164.3, 150.6, 148.0, 141.2, 121.7, 114.7, 105.1, 57.0, 51.1, 46.4, 44.7, 26.9; MS (Cl) m/z 289.2 (M+1); HPLC retention time=3.10 min. The hydrochloride salt was prepared by diluting in ethyl acetate and adding a 2.5 N HCl solution in ethyl acetate: mp=296.4° C.

EXAMPLE 22

4-(5-IODO-BENZOOXAZOL-2-YL)-1,4-DIAZA-BICYCLO[3.2.2]NONANE

The title compound was prepared from 5-iodo-2-methylsulfanyl-benzooxazole (prepared from 4-iodo-2-nitrophenol by the methods described in Examples 4, 5 and 7) by the procedure described in Example 9 in 38% yield: $^1$H NMR (CDCl$_3$, 400 MHz) δ 7.58 (d, 1H, J=1.2 Hz), 7.23 (dd, 1H, J=8.3, 1.7 Hz), 6.94 (d, 1H, J=8.3 Hz), 4.44–4.42 (m, 1H), 3.85 (t, 2H, J=5.8 Hz), 3.13–3.06 (m, 4H), 2.99–2.92 (m, 2H), 2.12–2.05 (m, 2H), 1.80–1.72 (m, 2H); $^{13}$C NMR (CDCl$_3$, 100 MHz) δ 162.0, 148.7, 146.0, 128.9, 124.9, 110.5, 87.2, 57.2, 50.5, 46.5, 44.4, 27.0; MS (Cl) m/z 370.0 (M+1); HPLC retention time=3.44 min. The hydrochloride salt was prepared by diluting in ethyl acetate and adding a 2.5 N HCl solution in ethyl acetate: mp>300° C.

EXAMPLE 23

4-(6-BROMO-OXAZOLO[5,4-b]PYRIDIN-2-YL)-1,4-DIAZA-BICYCLO[3.2.2]NONANE

The title compound was prepared from 6-bromo-2-methylsulfanyl-oxazolo[5,4-b]pyridine (prepared from 5-bromo-2-hydroxy-3-nitropyridine by the methods described in Examples 4, 5 and 7) by the procedure described in Example 9 in 64% yield: $^1$H NMR (CDCl$_3$, 400 MHz) δ 7.90 (d, 1H, J=2.1 Hz), 7.59 (d, 1H, J=2.1 Hz), 4.50–4.49 (m, 1H), 3.91 (t, 2H, J=5.8 Hz), 3.18–3.11 (m, 4H), 3.03–2.96 (m, 2H), 2.16–2.08 (m, 2H), 1.85–1.76 (m, 2H); $^{13}$C NMR (CDCl$_3$, 100 MHz) δ 161.4, 138.8, 125.3, 121.4, 116.7, 116.2, 57.0, 50.6, 46.4, 44.3, 26.8; MS (Cl) m/z 323.0 (M+1); HPLC retention time=3.08 min. The hydrochloride salt was prepared by diluting in ethyl acetate and adding a 2.5 N HCl solution in ethyl acetate: mp>300° C.

EXAMPLE 24

4-OXAZOLO[5,4-b]PYRIDIN-2-YL-1,4-DIAZA-BICYCLO[3.2.2]NONANE

The title compound was prepared from 2-(methylthio)oxazolo[5.4-b]pyridine (*J. Org. Chem.* 1995, 60, 5721) by the procedure described in Example 9 in 72% yield: $^1$H NMR (CDCl$_3$, 400 MHz) δ 7.83 (dd, 1H, J=5.0, 1.2 Hz), 7.47 (dd, 1H, J=7.5, 1.2 Hz), 7.04 (dd, J=7.5, 5.0 Hz), 4.49–4.47 (m, 1H), 3.89 (t, 2H, J=5.8 Hz), 3.13–3.05 (m, 4H), 3.00–2.92 (m, 2H), 2.13–2.06 (m, 2H), 1.81–1.72 (m, 2H); $^{13}$C NMR (CDCl$_3$, 100 MHz) δ 160.7, 158.4, 138.6, 136.3, 122.7, 120.7, 57.1, 50.4, 46.4, 44.2, 26.9; MS (Cl) m/z 245.2 (M+1). The hydrochloride salt was prepared by diluting in ethyl acetate and adding a 2.5 N HCl solution in ethyl acetate: mp>300° C.

EXAMPLE 25

4-OXAZOLO[5,4-C]PYRIDIN-2-YL-1,4-DIAZA-BICYCLO[3.2.2]NONANE

The title compound was prepared from 2-(methylthio)oxazolo[5,4-C]pyridine (*J. Org. Chem.* 1995, 60, 5721) by the procedure described in Example 9 in 67% yield: $^1$H NMR (CDCl$_3$, 400 MHz) δ 8.44 (s, 1H), 8.27 (d, 1H, J=5.0 Hz), 7.19 (d, 1H, J=5.3 Hz), 4.48 (s, 1H), 3.90 (t, 2H, J=5.8 Hz), 3.14–3.07 (m, 4H), 3.00–2.93 (m, 2H), 2.12–2.07 (m, 2H), 1.82–1.74 (m, 2H); $^{13}$C NMR (CDCl$_3$, 100 MHz) δ 163.4, 150.9, 147.5, 145.5, 129.8, 111.6, 62.3, 50.9, 46.4, 44.7, 30.3, 26.9; MS (Cl) m/z 245.2 (M+1); HPLC retention time=1.28 min. The hydrochloride salt was prepared by diluting in ethyl acetate and adding a 2.5 N HCl solution in ethyl acetate: mp>300° C.

EXAMPLE 26

4-OXAZOLO[4,5-C]PYRIDIN-2-YL-1,4-DIAZA-BICYCLO[3.2.2]NONANE

The title compound was prepared from 2-(methylthio)oxazolo[4.5-C]pyridine (*J. Org. Chem.* 1995, 60, 5721) by the procedure described in Example 9 in 32% yield: $^1$H NMR (CDCl$_3$, 400 MHz) δ 8.57 (s, 1H), 8.21 (d, 1H, J=5.4 Hz), 7.16 (d, 1H, J=5.4 Hz), 4.46–4.45 (m, 1H), 3.88 (t, 2H, J=5.8 Hz), 3.14–3.03 (m, 4H), 3.00–2.93 (m, 2H), 2.13–2.06 (m, 2H), 1.82–1.74 (m, 2H); $^{13}$C NMR (CDCl$_3$, 100 MHz) δ 161.6, 154.3, 142.0, 141.4, 138.0, 104.9, 62.3, 57.1, 50.8, 46.3, 44.6, 30.3, 26.9; MS (Cl) m/z 245.2 (M+1); HPLC retention time=1.28 min. The hydrochloride salt was prepared by diluting in ethyl acetate and adding a 2.5 N HCl solution in ethyl acetate: mp=288.5° C.

EXAMPLE 27

4-OXAZOLO[4,5-b]PYRIDIN-2-YL-1,4-DIAZA-BICYCLO[3.2.2]NONANE

The title compound was prepared from 2-(methylthio)oxazolo[4,5-b]pyridine (*J. Org. Chem.* 1995, 60, 5721) by the procedure described in Example 9 in 98% yield: $^1$H NMR CDCl$_3$, 400 MHz) δ 8.14 (dd, 1H, J=5.0, 1.2 Hz), 7.34 (dd, 1H, J=7.5, 1.2 Hz), 6.81 (dd, 1H, J=7.8, 5.0 Hz), 4.50 (s, 1H), 3.90 (t, 2H, J=5.8 Hz), 3.13–3.05 (m, 4H), 2.98–2.91 (m, 2H), 2.13–2.05 (m, 2H), 1.79–1.71 (m, 2H); $^{13}$C NMR CDCl$_3$, 100 MHz) δ 163.1, 158.7, 144.7, 141.4, 115.4, 114.8, 57.1, 50.6, 46.4, 46.3, 44.4, 30.3, 26.9; MS (Cl) m/z 245.2 (M+1); HPLC retention time=1.38 min. The hydrochloride salt was prepared by diluting in ethyl acetate and adding a 2.5 N HCl solution in ethyl acetate: mp>300° C.

EXAMPLE 28

2-AMINO-4-PYRIDIN-3-YL-PHENOL

Tetrakis(triphenylphosphine)palladium (139 mg, 0.12 mmol) was added to a flask containing 4-bromophenol (519 mg, 3.0 mmol), 3-pyridyl boronic acid (553 mg, 4.5 mmol) and sodium carbonate (1.27 g, 12.0 mmol). The flask was flushed with nitrogen and ethanol (6 mL) and water (0.6 mL) were added. The mixture was placed in an oil bath at 80° C. for 16 h. Upon cooling to RT the mixture was partitioned between water and chloroform. The aqueous layer was extracted with chloroform (3×) and the combined organic layers were dried (Na$_2$SO$_4$), filtered and concentrated. The crude residue was purified by chromatography (Biotage, 40S) eluting with 50% ethyl acetate in hexanes to afford 165 mg (32%) of 4-pyridin-3-yl-phenol as a white solid: mp=194.6° C., MS (Cl) m/z 172.1 (M+1).

Nitric acid (60 μL, 1.0 mmol) was added to a solution of 4-pyridin-3-yl-phenol (164 mg, 0.96 mmol) in acetic acid (2.8 mL). The mixture was heated at 60° C. for 30 min and the solution turned orange/brown in color. Upon cooling, water was added (3 mL) and 6 N NaOH (aq) was added until the solution was basic. The solution was extracted with ethyl acetate (3×) and then the aqueous phase was concentrated. The crude residue was washed with boiling methanol to afford 90 mg (43%) of 2-nitro-4-pyridin-3-yl-phenol as an orange solid: mp>300° C., MS (Cl) m/z 217.1 (M+1).

A mixture of 2-nitro-4-pyridin-3-yl-phenol (80 mg, 0.37 mmol), 10% Pd—C (8.0 mg), acetic acid (21 μL, 0.37 mmol) in MeOH (3.7 mL) was hydrogenated at 45 PSI at RT for 16 h. The mixture was filtered through a pad of celite and concentrate to afford 70 mg (100%) of the title compound as a brown oil: $^1$H NMR CDCl$_3$, 400 MHz) δ 8.57 (d, 1H, J=1.7 Hz), 8.30 (d, 1H, J=5.0 Hz), 7.75 (dt, 1H, J=7.9, 2.1 Hz), 7.25 (dd, 1H, J=7.9, 5.0 Hz), 6.77–6.69 (m, 2H), 3.94 (br s, 3H); $^{13}$C NMR CDCl$_3$, 100 MHz) δ 147.0, 146.5, 145.7, 137.6, 135.5, 134.8, 129.3, 124.0, 118.1, 115.4, 114.6; MS (Cl) m/z 187.1 (M+1); HPLC retention time=1.29 min.

EXAMPLE 29

4-(5-PYRIDIN-3-YL-BENZOOXAZOL-2-YL)-1,4-DIAZA-BICYCLO[3.2.2]NONANE

The title compound was prepared 2-methylsulfanyl-5-pyridin-3-yl-benzooxazole (prepared from 2-amino-4-pyridin-3-yl-phenol by the methods described in Examples 5 and 7) by the procedure described in Example 9 in 13% yield: $^1$H NMR CDCl$_3$, 400 MHz) δ 8.83 (d, 1H, J=2.1 Hz), 8.55 (dd, 1H, J=5.0, 1.6 Hz), 7.86–7.83 (m, 1H), 7.52 (d, 1H, J=1.6 Hz), 7.35–7.33 (m, 1H), 7.31 (d, 1H, J=8.3 Hz), 7.18 (dd, 1H, J=8.3, 1.6 Hz), 4.54–4.52 (m, 1H), 3.95 (t, 2H, J=5.8 Hz), 3.20–3.12 (m, 4H), 3.07–2.99 (m, 2H), 2.20–2.12 (m, 2H), 1.87–1.79 (m, 2H); $^{13}$C NMR CDCl$_3$, 100 MHz) δ 162.3, 149.1, 148.7, 148.3, 144.7, 137.3, 134.7, 134.4, 123.8, 119.7, 114.7, 109.1, 62.3, 57.2, 50.5, 46.5, 46.4, 44.4, 30.3, 27.0; MS (Cl) m/z 321.1 (M+1). The hydrochloride salt was prepared by diluting in ethyl acetate and adding a 2.5 N HCl solution in ethyl acetate: mp>300° C.

EXAMPLE 30

4-(1H-BENZOIMIDAZOL-2-YL)-1,4-DIAZA-BICYCLO[3.2.2]NONANE

Di-tert-butyl dicarbonate (600 mg, 2.75 mmol) was added to a solution of 2-chloroimidazole (381 mg, 2.50 mmol), and sodium hydroxide (120 mg, 3.0 mmol) in tetrahydrofuran (2.5 mL) and water (2.5 mL). After 3 h at RT an additional portion of di-tert-butyl dicarbonate (100 mg, 0.46 mmol) was added and the mixture was stirred at RT for 16 h. The mixture was extracted with ethyl acetate (3×) and the combined organic layers were dried (Na$_2$SO$_4$), filtered and concentrated to afford 627 mg (99%) of 2-chloro-benzoimidazole-1-carboxylic acid tert-butyl ester which was used without further purification: MS (Cl) m/z 253.1 (M+1).

2-Chloro-benzoimidazole-1-carboxylic acid tert-butyl ester (333 mg, 1.32 mmol), 1,4-diazabicyclo[3.2.2]nonane (57%, 195 mg, 0.88 mmol), tris(dibenzylideneacetone) dipalladium (28 mg, 0.031 mmol), racemic-2,2'-bis (diphenylphosphino)-1,1'-binaphthyl (58 mg, 0.093 mmol), sodium tert-butoxide (208 mg, 2.17 mmol) and toluene (1.55 mL) were added to a flame dried round bottom flask purged with nitrogen. The mixture was placed in an oil bath at 80° C. for 18 h and then cooled to RT. The mixture was filtered through a pad of celite and washed with chloroform and methanol. The filtrate was concentrated and the residue was purified by chromatography (Biotage, 12M) eluting with 8% methanol in chloroform with 20 drops of NH$_4$OH per liter of eluent to afford 104 mg (34%) of 2-(1,4-diaza-bicyclo[3.2.2] non-4-yl)-benzoimidazole-1-carboxylic acid tert-butyl ester: MS (Cl) m/z 343.1 (M+1).

1 N Hydrochloric acid (3 mL, in methanol) was added to of 2-(1,4-diaza-bicyclo[3.2.2]non-4-yl)-benzoimidazole-1-carboxylic acid tert-butyl ester (104 mg, 0.304 mmol). The mixture was stirred at RT for 18 h and concentrated. The residue was diluted with 1 N hydrochloric acid (3 mL, aq.) and extracted with ethyl acetate (3×). The aqueous layer was treated with 6 N sodium hydroxide (3 mL, aq.) and extracted with chloroform (6×). The combined organic layers were dried (Na$_2$SO$_4$), filtered and concentrated to afford 50 mg (68%) of the title compound: $^1$H NMR (CD$_3$OD, 400 MHz) δ 7.19 (dd, 2H, J=5.8 Hz, 3.3 Hz), 6.95 (dd, 2H, J=5.8, 2.9 Hz), 4.98 (br s, 1H), 4.27–4.24 (m, 1H), 3.83 (t, 2H, J=5.8 Hz), 3.09–2.91 (m, 6H), 2.16–2.08 (m, 2H), 1.87–1.78 (m, 2H); MS (Cl) m/z 243.3 (M+1). The hydrochloride salt was prepared by diluting in ethyl acetate and adding a 2.5 N HCl solution in ethyl acetate: mp>300° C.

EXAMPLE 31

4-(4-NITRO-BENZOOXAZOL-2-YL)-1,4-DIAZA-BICYCLO[3.2.2]NONANE

The title compound was prepared from 2-methylsulfanyl-4-nitro-benzooxazole (prepared from 2-amino-3-nitrophenol by the methods described in Example 5 and Example 7) by the procedure described in Example 9 in 79% yield: $^1$H NMR CDCl$_3$, 400 MHz) δ 7.84 (dd, 1H, J=8.7, 0.8 Hz), 7.36 (dd, 1H, J=7.5, 0.8 Hz), 6.92 (t, 1H, J=8.3 Hz), 4.51 (s, 1H), 3.93–3.91 (m, 2H), 3.06–2.99 (m, 4H), 2.94–2.87 (m, 2H), 2.07–2.01 (m, 2H), 1.83–1.74 (m, 2H); $^{13}$C NMR CDCl$_3$, 100 MHz) δ 163.9, 151.0, 140.3, 133.5, 120.2, 119.2, 113.9, 56.3, 50.6, 45.9, 44.1, 26.3; MS (Cl)

m/z 289.2 (M+1); HPLC retention time=3.02 min. The hydrochloride salt was prepared by diluting in ethyl acetate and adding a 2.5 N HCl solution in ethyl acetate: mp=232.1° C.

EXAMPLE 32

4-(5-NITRO-BENZOOXAZOL-2-YL)-1,4-DIAZA-BICYCLO[3.2.2]NONANE

The title compound was prepared from 2-methylsulfanyl-5-nitro-benzooxazole (prepared from 2-amino-4-nitrophenol by the methods described in Example 5 and Example 7) by the procedure described in Example 9 in 36% yield: $^1$H NMR CDCl$_3$, 400 MHz) δ 7.84 (d, 1H, J=2.1 Hz), 7.97 (dd, 1H, J=8.7, 2.1 Hz), 7.28 (d, 1H, J=8.7 Hz), 4.56–4.55 (m, 1H), 3.97 (t, 2H, J=5.8 Hz), 3.23–3.16 (m, 4H), 3.08–3.01 (m, 2H), 2.23–2.15 (m, 2H), 1.94–1.85 (m, 2H); $^{13}$C NMR CDCl$_3$, 100 MHz) δ 163.1, 152.8, 145.2, 144.3, 117.2, 111.7, 108.5, 56.4, 50.5, 45.9, 43.8, 26.3; MS (Cl) m/z 289.2 (M+1); HPLC retention time=3.11 min. The hydrochloride salt was prepared by diluting in ethyl acetate and adding a 2.5 N HCl solution in ethyl acetate: mp=240.2° C.

EXAMPLE 33

4-(5-METHYL-BENZOOXAZOL-2-YL)-1,4-DIAZA-BICYCLO[3.2.2]NONANE

The title compound was prepared from 5-methyl-2-methylsulfanyl-benzooxazole (prepared from 2-amino-4-methylphenol by the methods described in Example 5 and Example 7) by the procedure described in Example 9 in 4% yield: $^1$H NMR (CDCl$_3$, 400 MHz) δ 7.14 (s, 1H), 7.10 (d, 1H, J=7.9 Hz), 6.80 (dd, 1H, J=7.9, 0.8Hz), 4.55–4.53 (m, 1H), 3.95 (t, 2H, J=5.8 Hz), 3.24–3.17 (m, 4H), 3.10–3.03 (m, 2H), 2.38 (s, 3H), 2.22–2.15 (m, 2H), 1.89–1.81 (m, 2H); MS (Cl) m/z 258.2 (M+1). The hydrochloride salt was prepared by diluting in ethyl acetate and adding a 2.5 N HCl solution in ethyl acetate: mp=220.2° C.

EXAMPLE 34

4-(6-METHYL-BENZOOXAZOL-2-YL)-1,4-DIAZA-BICYCLO[3.2.2]NONANE

The title compound was prepared from 6-methyl-2-methylsulfanyl-benzooxazole (prepared from 2-amino-5-methylphenol by the methods described in Example 5 and Example 7) by the procedure described in Example 9 in 2% yield: $^1$H NMR CDCl$_3$, 400 MHz) δ 7.21 (d, 1H, J=7.9 Hz), 7.06 (s, 1H), 6.96 (d, 1H, J=8.3 Hz), 4.55–4.52 (m, 1H), 3.94 (t, 2H, J=5.8 Hz), 3.23–3.15 (m, 4H), 3.09–3.01 (m, 2H), 2.39 (s, 3H), 2.22–2.14 (m, 2H), 1.89–1.80 (m, 2H); MS (Cl) m/z 258.2 (M+1). The hydrochloride salt was prepared by diluting in ethyl acetate and adding a 2.5 N HCl solution in ethyl acetate.

EXAMPLE 35

4-(5-METHYL-OXAZOLO[4,5-b]PYRIDIN-2-YL)-1,4-DIAZA-BICYCLO[3.2.2]NONANE

The title compound was prepared from 5-methyl-2-methylsulfanyl-oxazolo[4,5-b]pyridine (prepared from 6-methyl-2-nitro-pyridin-3-ol by the methods described in Examples 4, 5 and 7) by the procedure described in Example 9 in 67% yield: $^1$H NMR CDCl$_3$, 400 MHz) δ 7.22 (d, 1H, J=7.9 Hz), 6.65 (d, 1H, J=7.9 Hz), 4.49 (s, 1H), 3.89 (t, 2H, J=5.8 Hz), 3.13–3.05 (m, 4H), 2.99–2.90 (m, 2H), 2.47 (s, 3H), 2.13–2.06 (m, 2H), 1.78–1.70 (m, 2H), $^{13}$C NMR CDCl$_3$, 100 MHz) δ 163.3, 158.2, 153.5, 139.8, 114.9, 114.3, 57.1, 50.5, 46.4, 44.3, 26.9, 24.1; MS (Cl) m/z 259.2 (M+1); HPLC retention time=2.08 min. The hydrochloride salt was prepared by diluting in ethyl acetate and adding a 2.5 N HCl solution in ethyl acetate: mp=287.5° C.

EXAMPLE 36

4-(6-CHLORO-5-NITRO-BENZOOXAZOL-2-YL)-1,4-DIAZA-BICYCLO[3.2.2]NONANE

The title compound was prepared from 6-chloro-2-methylsulfanyl-5-nitro-benzooxazole (prepared from 2-amino-5-chloro-4-nitrophenol by the methods described in Example 5 and Example 7) by the procedure described in Example 9 in 74% yield: $^1$H NMR (CDCl$_3$, 400 MHz) δ 8.02 (d, 1H, J=2.1 Hz), 7.95 (d, 1H, J=2.1 Hz), 4.56–4.54 (m, 1H), 3.97 (t, 2H, J=5.8 Hz), 3.23–3.12 (m, 4H), 3.08–3.01 (m, 2H), 2.20–2.14 (m, 2H), 1.91–1.83 (m, 2H); MS (Cl) m/z 323.1 (M+1). The hydrochloride salt was prepared by diluting in ethyl acetate and adding a 2.5 N HCl solution in ethyl acetate: mp=242.3° C.

EXAMPLE 37

4-(5,7-DICHLORO-BENXOOXAZOL-2-YL)-1,4-DIAZA-BICYCLO[3.2.2]NONANE

The title compound was prepared from 5,7-dichloro-2-methylsulfanyl-benzooxazole (prepared from 2-amino-4,6-dichlorophenol by the methods described in Example 5 and Example 7) by the procedure described in Example 9 in 71% yield: $^1$H NMR CDCl$_3$, 400 MHz) δ 7.17 (d, 1H, J=1.3 Hz), 6.98 (d, 1H, J=1.3 Hz), 4.57 (s, 1H), 3.99 (t, 2H, J=5.8 Hz), 3.30–3.23 (m, 4H), 3.15–3.08 (m, 2H), 2.24–2.17 (m, 2H), 1.95–1.86 (m, 2H); MS (Cl) m/z 312.1 (M+1). The hydrochloride salt was prepared by diluting in ethyl acetate and adding a 2.5 N HCl solution in ethyl acetate: mp=251.2° C.

EXAMPLE 38

4-(5-CHLORO-6-NITRO-BENZOOXAZOL-2-YL)-1,4-DIAZABICYCLO[3.2.2]NONANE

The title compound was prepared 5-chloro-2-methylsulfanyl-6-nitro-benzooxazole (prepared from 2-amino-4-chloro-5-nitrophenol by the methods described in Example 5 and Example 7) by the procedure described in Example 9 in 30% yield: MS (Cl) m/z 323.1 (M+1). The hydrochloride salt was prepared by diluting in ethyl acetate and adding a 2.5 N HCl solution in ethyl acetate: mp>300° C.

EXAMPLE 39

4-(5-AMINO-BENZOOXAZOL-2-YL)-1,4-DIAZA-BICYCLO[3.2.2]NONANE

10% Palladium on carbon (300 mg) was added to a solution of 4-(5-nitro-benzooxazol-2-yl)-1,4-diaza-bicyclo [3.2.2]nonane (288 mg, 1 mmol, prepared as in Example 21) in ethanol (5 mL) and subjected to hydrogen gas at 50 PSI at RT for a period of 16 h. The reation mixture was diluted with ethanol (20 mL) and filtered through a pad of celite. Concentration in vacuo gave 209 mg of the title compound as a brown oil: $^1$H NMR (CD$_3$OD, 400 MHz) δ 7.06 (d, 1H, J=8.3 Hz), 6.75 (d, 1H, J=1.3 Hz), 6.50 (dd, 1H, J=8.3, 1.3 Hz), 4.56 (br s, 1H), 4.08 (br s, 2H), 3.62–3.47 (m, 6H), 2.34–2.31 (m, 2H), 2.20–2.16 (m, 2H); MS (Cl) m/z 259.2 (M+1).

EXAMPLE 40

BENZYL-[2-(1,4-DIAZA-BICYCLO[3.2.2]NON-4-YL)-BENZOOXAZOL-5-YL]-AMINE

Sodium triacetoxyborohydride (118 mg, 0.56 mmol) was added to a solution of 4-(5-amino-benzooxazol-2-yl)-1,4-diaza-bicyclo[3.2.2]nonane (52 mg, 0.20 mmol, prepared as in Example 39) and benzaldehyde (21 µL, 0.204 mmol) in 1,2-dichloroethane. The resulting mixture was allowed to stir at RT for a period of 3 h. at which time 2 mL of 1 N NaOH solution was added. The aqueous layer was extracted with $CDCl_3$ (3×) and the combined organic layers were washed with water and brine and then dried ($Na_2SO_4$), filtered and concentrated. The crude residue was purified by chromatography (Biotage, 25M) eluting with 6% MeOH in $CDCl_3$ containing 1 mL of $NH_4OH$ per L of eluent to give 37 mg of the title compound as an oil: $^1H$ NMR $CDCl_3$, 400 MHz) δ 7.37–7.29 (m, 3H), 7.25–7.22 (m, 2H), 7.00 (d, 1H, J=8.7 Hz), 6.64 (d, 1H, J=2.1 Hz), 6.27 (dd, 1H, J=8.7, 2.1 Hz), 4.47–4.45 (m, 1H), 4.30 (s, 2H), 3.87 (t, 2H, J=5.8 Hz), 3.16–3.09 (m, 4H), 3.01–2.96 (m, 2H), 2.15–2.08 (m, 2H), 1.81–1.73 (m, 2H): $^{13}C$ NMR ($CDCl_3$, 100 MHz) δ 146.0, 145.1, 142.0, 139.8, 128.8, 127.7, 127.3, 108.8, 106.0, 100.6, 57.3, 50.1, 49.4, 46.5, 44.1, 27.0; MS (Cl) m/z 349.2 (M+1).

EXAMPLE 41

[2-(1,4-DIAZA-BICYCLO[3.2.2]NON-4-YL)-BENZOOXAZOL-5-YL]-(3-PHENYL-ALLYL)-AMINE

The title compound was prepared according to the procedure in Example 40 using trans-cinnamaldehyde in 42% yield: MS (Cl) m/z 375.2 (M+1).

EXAMPLE 42

[2-(1,4-DIAZA-BICYCLO[3.2.2]NON-4-YL)-BENZOOXAZOL-5-YL]-PYRIDIN-3-YLMETHYL-AMINE

The title compound was prepared according to the procedure in Example 40 using 3-pyridinecarboxaldehyde in 52% yield: MS (Cl) m/z 350.2 (M+1).

EXAMPLE 43

DIBENZYL-[2-(1,4-DIAZA-BICYCLO[3.2.2]NON-4-YL)-BENZOOXAZOL-5-YL]-AMINE

The title compound was prepared according to the procedure in Example 40 using 2.2 equivalents of benzaldehyde in 10% yield: $^1H$ NMR $CDCl_3$, 400 MHz) δ 7.37–7.20 (m, 10H), 7.01 (d, 1H, J=8.7 Hz), 6.76 (d, 1H, J=2.1 Hz), 6.39 (dd, 1H, J=8.7, 2.5 Hz), 4.63 (s, 4H), 4.50 (br s, 1H), 3.91–3.89 (m, 2H), 3.20–3.10 (m, 4H), 3.05–2.95 (m, 2H), 2.20–2.10 (m, 2H), 1.90–1.80 (m, 2H); MS (Cl) m/z 439.2 (M+1).

EXAMPLE 44

4-(5-m-TOLYL-BENZOOXAZOL-2-YL)-1,4-DIAZA-BICYCLO[3.2.2]NONANE $Et_3N$ (5 µL) was added to a solution of palladium (II) acetate (0.7 mg, 3.1 µmol) and 2-(N,N-dimethylamino)-2'-dicyclohexylphosphinobiphenyl (1.8 mg, 4.65 µmol) in 1,2-dimethoxyethane (0.5 mL) under a nitrogen atmosphere at RT. 4-(5-Bromo-benzooxazol-2-yl)-1,4-diaza-bicyclo[3.2.2]nonane (50 mg, 0.155 mmol, prepared in example 9), m-tolylboronic acid (32 mg, 0.233 mmol) and CsF (70 mg, 0.465 mmol) were added to the solution and the mixture was heated in an oil bath (temp=80° C.) for a period of 16 h. The reaction mixture was cooled to RT, filtered through a pad of celite and concentrated in vacuo. The crude residue was purified by chromatography (Biotage, 12L) eluting with 4% MeOH in $CDCl_3$ with 1 mL of $NH_4OH$ per L to give 39 mg (75%) of the title compound as a film: $^1H$ NMR $CDCl_3$, 400 MHz) δ 7.55 (d, 1H, J=1.7 Hz), 7.40–7.38 (m, 2H), 7.33–7.26 (m, 2H), 7.22–7.19 (m, 1H), 7.14 (d, 1H, J=7.4 Hz), 4.54–4.52 (m, 1H), 3.94 (t, 2H, J=5.8 Hz), 3.19–3.12 (m, 4H), 3.06–2.99 (m, 2H), 2.41 (s, 3H), 2.20–2.13 (m, 2H), 1.86–1.78 (m, 2H); $^{13}C$ NMR $CDCl_3$, 100 MHz) δ 162.2, 148.6, 144.3, 141.9, 138.5, 138.0, 128.9, 128.4, 127.8, 124.6, 119.8, 114.8,108.7, 57.3, 50.4, 46.5, 44.4, 27.0, 21.8; MS (Cl) m/z 334,1 (M+1).

EXAMPLE 45

4-(6-PHENYL-OXAZOLO[5,4-b]PYRIDIN-2-YL)-1,4-DIAZA-BICYCLO[3.2.2]NONANE

The title compound was prepared according to the procedure in Example 44 using phenylboronic acid and 4-(6-bromo-oxazolo[5,4-b]pyridin-2-yl)-1,4-diaza-bicyclo[3.2.2]nonane (prepared in Example 23) in 50% yield as a colorless oil: $^1H$ NMR ($CDCl_3$, 400 MHz) δ 8.10 (d, 1H, J=2.1 Hz), 7.72 (d, 1H, J=2.1 Hz), 7.57–7.55 (m, 2H), 7.47–7.44 (m, 2H), 7.39–7.36 (m, 1H), 4.58 (br s, 1H), 3.98 (t, 2H, J=5.8 Hz), 3.22–3.14 (m, 4H), 3.11–3.01 (m, 2H), 2.22–2.15 (m, 2H), 1.89–1.82 (m, 2H); MS (Cl) m/z 321.2 (M+1).

EXAMPLE 46

4-[5-(4-TRIFLUOROMETHYL-PHENYL)-BENZOOXAZOL-2-YL]-1,4-DIAZA-BICYCLO[3.2.2]NONANE

The title compound was prepared according to the procedure in Example 44 using 4-trifluoromethyl-phenylboronic acid and 4-(5-bromo-benzooxazol-2-yl)-1,4-diaza-bicyclo[3.2.2]nonane in 54% yield: MS (Cl) m/z 388.4 (M+1).

EXAMPLE 47

4-(6-BROMO-OXAZOLO[4,5-b]PYRIDIN-2-YL)-1,4-DIAZA-BICYCLO[3.2.2]NONANE

Bromine (0.12 mL, 2.29 mmol) was added to a solution of 4-oxazolo[4,5-b]pyridin-2-yl-1,4-diaza-bicyclo[3.2.2]nonane (560 mg, 2.29 mmol, prepared in Example 27) and sodium acetate (2.26 g, 27.5 mmol) in water (12 mL) and acetic acid (12 mL). The resulting mixture was heated to reflux for 2 h. The mixture was cooled and extracted with ethyl acetate (3×). The combined organic layers were washed with water (2×) and brine (1×) and dried over sodium sulfate, filtered and concentrated. The crude residue was purified by chromatography (Biotage, 25M) using a gradient elution from 4% $MeOH/CDCl_3$ containing 0.1% $NH_4OH$ to 8% $MeOH/CDCl_3$ containing 0.1% $NH_4OH$ giving 578 mg (78%) of the title compound as an oil: $^1H$ NMR $CDCl_3$, 400 MHz) δ 8.23 (d, 1H, J=1.7 Hz), 7.50 (d, 1H, J=1.7 Hz), 4.51 (br s, 1H), 3.92 (br s, 2H), 3.16–3.04 (m, 4H), 3.02–2.94 (m, 2H), 2.17–2.01 (m, 2H), 1.83–1.74 (m, 2); MS (Cl) m/z 325.0/323.0 (M+1).

EXAMPLE 48

4-(6-PHENYL-OXAZOLO[4,5-b]PYRIDIN-2-YL)-1,4-DIAZA-BICYCLO[3.2.2]NONANE

The title compound was prepared according to the procedure detailed in Example 44 using phenyl boronic acid and 4-(6-bromo-oxazolo[4,5-b]pyridin-2-yl)-1,4-diazabicyclo[3.2.2]nonane (prepared in Example 47) in 27% yield: $^1$H NMR CDCl$_3$, 400 MHz) δ 8.48 (d, 1H, J=2.1 Hz), 7.62 (d, 1H, J=2.1 Hz), 7.57–7.55 (m, 2H), 7.47–7.43 (m, 2H), 7.40–7.34 (m, 1H), 4.62 (br s, 1H), 4.00 (t, 2H, J=5.8 Hz), 3.20–3.15 (m, 4H), 3.08–3.01 (m, 2H), 2.19–2.08 (m, 2H), 1.90–1.81 (m, 2H); MS (Cl) m/z 321.2 (M+1).

What is claimed is:

1. A compound of the formula

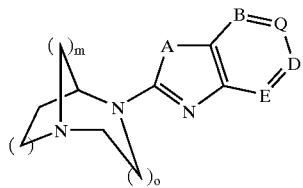

I wherein n=1 or 2;
m=1;
o=1 or 2;
A=O, S or NR$^1$;
B=N or CR$^2$;
Q=N or CR$^3$;
D=N or CR$^4$;
E=N or CR$^5$;
R$^1$ is H, a straight chain or branched (C$_1$–C$_8$)alkyl, C(=O)OR$^6$, CH$_2$R$^6$, C(=O)NR$^6$R$^7$, C(=O)R$^6$, or SO$_2$R$^6$;
each R$^2$, R$^3$, R$^4$ and R$^5$ is independently selected from F, Cl, Br, I, nitro, cyano, CF$_3$, —NR$^6$R$^7$, —NR$^6$C(=O)R$^7$, —NR$^6$C(=O)NR$^7$R$^8$, —NR$^6$C(=O)OR$^7$, —NR$^6$S(=O)$_2$R$^7$, —NR$^6$S(=O)$_2$NR$^7$R$^8$, —OR$^6$, —OC(=O)R$^6$, —OC(=O)OR$^6$, —OC(=O)NR$^6$R$^7$, —OC(=O)SR$^6$, —C(=O)OR$^6$, —C(=O)R$^6$, —C(=O)NR$^6$R$^7$, —SR$^6$, —S(=O)R$^6$, —S(=O)$_2$R$^6$, —S(=O)$_2$NR$^6$R$^7$, and R$^6$;
each R$^6$, R$^7$, and R$^8$ is independently selected from H, straight chain or branched (C$_1$–C$_8$)alkyl, straight chain or branched (C$_2$–C$_8$)alkenyl, straight chain or branched (C$_2$–C$_8$)alkynyl, (C$_3$–C$_8$)cycloalkyl, (C$_4$–C$_8$) cycloalkenyl, 3–8 membered heterocycloalkyl groups selected from aziridinyl, azetidinyl, pyrrolidinyl, piperidinyl, azepinyl, piperazinyl, 1,2,3,6-tetrahydropyridinyl, oxiranyl, oxetanyl, tetrahydrofuranyl, tetrahydropyranyl, tetrahydrothienyl, tetrahydrothiopyranyl, piperidino, morpholino, thiomorpholino, thioxanyl, pyrrolinyl, indolinyl, 2H-pyranyl, 4H-pyranyl, dioxanyl, 1,3-dioxolanyl, pyrazolinyl, dihydropyranyl, dihydrothienyl, dihydrofuranyl, pyrazolidinyl, imidazolinyl, imidazolidinyl, 3-azabicyclo[3.1.0] hexanyl, 3-azabicyclo[4.1.0]heptanyl, 3H-indolyl, quinuclidinyl and quinolizinyl, (C$_5$–C$_{11}$)bicycloalkyl, (C$_7$–C$_{11}$)bicycloalkenyl, 5–11 membered heterobicycloalkyl groups consisting of non-aromatic two-ringed cyclic groups, wherein at least one of the rings contains a heteroatom selected from O, S, or N, 5–11 membered heterobicycloalkenyl groups consisting of non-aromatic two-ringed cyclic groups, wherein at least one of the rings contains a heteroatom selected from O, S, or N and at least one endocyclic or exocyclic double bond, (C$_6$–C$_{11}$) aryl, and 5–12 membered heteroaryls selected from pyridinyl, pyridazinyl, imidazolyl, pyrimidinyl, pyrazolyl, triazolyl, pyrazinyl, quinolyl, isoquinolyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, purinyl, oxadiazolyl, thiazolyl, thiadiazolyl, furazanyl, benzofurazanyl, benzothiophenyl, benzotriazolyl, benzothiazolyl, benzoxazolyl, quinazolinyl, quinoxalinyl, naphthyridinyl, dihydroquinolyl, tetrahydroquinolyl, dihydroisoquinolyl, tetrahydroisoquinolyl, benzofuryl, furopyridinyl, pyrolopyrimidinyl, and azaindolyl; wherein each R$^6$, R$^7$, and R$^8$ is optionally substituted with from one to six substituents, independently selected from F, Cl, Br, I, nitro, cyano, CF$_3$, —NR$^9$R$^{10}$, —NR$^9$C(=O)R$^{10}$, —NR$^9$C(=O)NR$^{10}$R$^{11}$, —NR$^9$C(=O)OR$^{10}$, —NR$^9$S(=O)$_2$R$^{10}$, —NR$^9$S(=O)$_2$NR$^{10}$R$^{11}$, —OR$^9$, —OC(=O)R$^9$, —OC(=O)OR$^9$, —OC(=O)NR$^9$R$^{10}$, —OC(=O)SR$^9$, —C(=O)OR$^9$, —C(=O)R$_9$, —C(=O)NR$^9$R$^{10}$, —SR$^9$, —S(=O)R$^9$, —S(=O)$_2$R$^9$, —S(=O)$_2$NR$^9$R$^{10}$ and R$^9$;
each R$^9$, R$^{10}$ and R$^{11}$ is independently selected from H, straight chain or branched (C$_1$–C$_8$)alkyl, straight chain or branched (C$_2$–C$_8$)alkenyl, straight chain or branched (C$_2$–C$_8$)alkynyl, (C$_3$–C$_8$)cycloalkyl, (C$_4$–C$_8$) cycloalkenyl, 3–8 membered heterocycloalkyl groups selected from aziridinyl, azetidinyl, pyrrolidinyl, piperidinyl, azepinyl, piperazinyl, 1,2,3,6-tetrahydropyridinyl, oxiranyl, oxetanyl, tetrahydrofuranyl, tetrahydropyranyl, tetrahydrothienyl, tetrahydrothiopyranyl, piperidino, morpholino, thiomorpholino, thioxanyl, pyrrolinyl, indolinyl, 2H-pyranyl, 4H-pyranyl, dioxanyl, 1,3-dioxolanyl, pyrazolinyl, dihydropyranyl, dihydrothienyl, dihydrofuranyl, pyrazolidinyl, imidazolinyl, imidazolidinyl, 3-azabicyclo[3.1.0] hexanyl, 3-azabicyclo[4.1.0]heptanyl, 3H-indolyl, quinuclidinyl and quinolizinyl, (C$_5$–C$_{11}$)bicycloalkyl, (C$_7$–C$_{11}$)bicycloalkenyl, 5–11 membered heterobicycloalkyl groups consisting of non-aromatic two-ringed cyclic groups, wherein at least one of the rings contains a heteroatom selected from O, S, or N, 5–11 membered heterobicycloalkenyl groups consisting of non-aromatic two-ringed cyclic groups, wherein at least one of the rings contains a heteroatom selected from O, S, or N and at least one endocyclic or exocyclic double bond, (C$_6$–C$_{11}$)aryl or 5–12 membered heteroaryls selected from pyridinyl, pyridazinyl, imidazolyl, pyrimidinyl, pyrazolyl, triazolyl, pyrazinyl, quinolyl, isoquinolyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, purinyl, oxadiazolyl, thiazolyl, thiadiazolyl, furazanyl, benzofurazanyl, benzothiophenyl, benzotriazolyl, benzothiazolyl, benzoxazolyl, quinazolinyl, quinoxalinyl, naphthyridinyl, dihydroquinolyl, tetrahydroquinolyl, dihydroisoquinolyl, tetrahydroisoquinolyl, benzofuryl, furopyridinyl, pyrolopyrimidinyl, and azaindolyl; wherein each R$^9$, R$^{10}$ and R$^{11}$ is optionally substituted with from one to six substituents independently selected from F, Cl, Br, I, nitro, cyano, CF$_3$, —NR$^{12}$R$^{13}$, —NR$^{12}$C(=O)R$^{13}$, —NR$^{12}$C(=O) NR$^{13}$R$^{14}$, —NR$^{12}$C(=O)OR$^{13}$, —NR$^{12}$S(=O)$_2$R$^{13}$, —NR$^{12}$S(=O)$_2$NR$^{13}$R$^{14}$, —OR$^{12}$, —OC(=O)R$^{12}$, —OC(=O)OR$^{12}$, —OC(=O)NR$^{12}$R$^{13}$, —OC(=O)

$SR^{12}$, $-C(=O)OR^{12}$, $-C(=O)R^{12}$, $-C(=O)NR^{12}R^{13}$, $-SR^{12}$, $S(=O)R^{12}$, $-S(=O)_2R^{12}$, $-S(=O)_2NR^{12}R^{13}$ and $R^{12}$;

each $R^{12}$, $R^{13}$, and $R^{14}$ is independently selected from H, straight chain or branched ($C_1$–$C_8$)alkyl, straight chain or branched ($C_2$–$C_8$)alkenyl, straight chain or branched ($C_2$–$C_8$)alkynyl, ($C_3$–$C_8$)cycloalkyl, ($C_4$–$C_8$) cycloalkenyl, 3–8 membered heterocycloalkyl groups selected from aziridinyl, azetidinyl, pyrrolidinyl, piperidinyl, azepinyl, piperazinyl, 1,2,3,6-tetrahydropyridinyl, oxiranyl, oxetanyl, tetrahydrofuranyl, tetrahydropyranyl, tetrahydrothienyl, tetrahydrothiopyranyl, piperidino, morpholino, thiomorpholino, thioxanyl, pyrrolinyl, indolinyl, 2H-pyranyl, 4H-pyranyl, dioxanyl, 1,3-dioxolanyl, pyrazolinyl, dihydropyranyl, dihydrothienyl, dihydrofuranyl, pyrazolidinyl, imidazolinyl, imidazolidinyl, 3-azabicyclo[3.1.0] hexanyl, 3-azabicyclo[4.1.0]heptanyl, 3H-indolyl, quinuclidinyl and quinolizinyl, ($C_5$–$C_{11}$)bicycloalkyl, ($C_7$–$C_{11}$)bicycloalkenyl, 5–11 membered heterobicycloalkyl groups consisting of non-aromatic two-ringed cyclic groups, wherein at least one of the rings contains a heteroatom selected from O, S, or N, 5–11 membered heterobicycloalkenyl groups consisting of non-aromatic two-ringed cyclic groups, wherein at least one of the rings contains a heteroatom selected from O, S, or N and at least one endocyclic or exocyclic double bond, ($C_6$–$C_{11}$)aryl and 5–12 membered heteroaryls selected from pyridinyl, pyridazinyl, imidazolyl, pyrimidinyl, pyrazolyl, triazolyl, pyrazinyl, quinolyl, isoquinolyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, purinyl, oxadiazolyl, thiazolyl, thiadiazolyl, furazanyl, benzofurazanyl, benzothiophenyl, benzotriazolyl, benzothiazolyl, benzoxazolyl, quinazolinyl, quinoxalinyl, naphthyridinyl, dihydroquinolyl, tetrahydroquinolyl, dihydroisoquinolyl, tetrahydroisoquinolyl, benzofuryl, furopyridinyl, pyrolopyrimidinyl, and azaindolyl;

or $R^2$ and $R^3$, or $R^3$ and $R^4$, or $R^4$ and $R^5$, may form another 6-membered aromatic or heteroaromatic ring sharing B and Q, or Q and D, or D and E, respectively, and may be optionally substituted with from one to four substituents independently selected from the group of radicals set forth in the definition of $R^6$, $R^7$ and $R^8$ above;

or an enantiomeric, diastereomeric, or tautomeric isomer thereof, or a pharmaceutically acceptable salt of such compound or isomer.

2. A compound according to claim 1 wherein A=S.

3. A compound according to claim 1 wherein A=O.

4. A compound according to claim 3 wherein B=$CR^2$, Q=$CR^3$, D=$CR^4$, E=$CR^5$.

5. A compound according to claim 3 wherein B=N, Q=$CR^3$, D=$CR^4$, and E=$CR^5$.

6. A compound according to claim 3 wherein B=$CR^2$, Q=N, D=$CR^4$, and E=$CR^5$.

7. A compound according to claim 3 wherein B=$CR^2$, Q=$CR^3$, D=N, and E=$CR^5$.

8. A compound according to claim 3 wherein B=$CR^2$, Q=$CR^3$, D=$CR^4$, and E=N.

9. A pharmaceutical composition for the treatment of schizophrenia in a mammal, comprising an amount of a compound according to claim 1 that is effective in treating schizophrenia and a pharmaceutically acceptable carrier.

10. A method of treating schizophrenia in a mammal, comprising administering to said mammal an amount of a compound according to claim 1 that is effective in treating schizophrenia.

* * * * *